US012053262B2

(12) United States Patent
Strasfeld et al.

(10) Patent No.: US 12,053,262 B2
(45) Date of Patent: Aug. 6, 2024

(54) SKIN DIAGNOSTICS USING OPTICAL SIGNATURES

(71) Applicant: Precision Healing, Inc., Newton, MA (US)

(72) Inventors: David B Strasfeld, Somerville, MA (US); Ira M Herman, Boston, MA (US); W David Lee, Brookline, MA (US); Ryan Daniel Williams, Somerville, MA (US); Sean P Madden, Arlington, MA (US)

(73) Assignee: Precision Healing LLC, Newton, MA (US)

( * ) Notice: Subject to any disclaimer, the term of this patent is extended or adjusted under 35 U.S.C. 154(b) by 282 days.

(21) Appl. No.: 17/155,141

(22) Filed: Jan. 22, 2021

(65) Prior Publication Data

US 2021/0228083 A1 Jul. 29, 2021

Related U.S. Application Data

(60) Provisional application No. 62/964,969, filed on Jan. 23, 2020, provisional application No. 63/132,541, filed on Dec. 31, 2020.

(51) Int. Cl.
*A61B 5/00* (2006.01)
*A61B 5/145* (2006.01)
(Continued)

(52) U.S. Cl.
CPC .......... *A61B 5/0071* (2013.01); *A61B 5/0075* (2013.01); *A61B 5/14546* (2013.01);
(Continued)

(58) Field of Classification Search
CPC . A61B 5/0071; A61B 5/0075; A61B 5/14546; A61B 5/1455; A61B 5/443;
(Continued)

(56) References Cited

U.S. PATENT DOCUMENTS 5,553,616 A * 9/1996 Ham .................... A61B 5/6838
250/341.1
5,701,902 A * 12/1997 Vari .................... A61B 5/0075
600/476

(Continued)

OTHER PUBLICATIONS

Niu, L., Zhao, F., Chen, J., Nong, J., Wang, C., Wang, J., . . . & Hu, S. (2018). Isothermal amplification and rapid detection of Klebsiella pneumoniae based on the multiple cross displacement amplification (MCDA) and gold nanoparticle lateral flow biosensor (LFB). Plos one, 13(10), e0204332.

(Continued)

*Primary Examiner* — Sanjay Cattungal
(74) *Attorney, Agent, or Firm* — Adams Intellex, PLC

(57) ABSTRACT

Disclosed techniques include skin diagnostics using optical signatures. A plurality of optical excitation light wavelength bands is scanned on a material sample, wherein the material sample exhibits optical spectral characteristics along the light wavelength spectrum. Excitation response wavelengths emitted by the material sample are captured in response to the plurality of optical excitation light wavelength bands, wherein the capturing is accomplished using an imaging sensor. Output values of a plurality of pixels of an image from the imaging sensor are measured, wherein the image represents excitation response wavelengths captured by the imaging sensor, wherein the measuring detects optical spectral characteristics of the material sample, and wherein the optical spectral characteristics are in response to the plurality of optical excitation light wavelength bands. An output signature indicative of composition of the material sample is generated, wherein the output signature is based on interpreting the output values that were measured.

31 Claims, 17 Drawing Sheets

(51) Int. Cl.

| | |
|---|---|
| *A61B 5/1455* | (2006.01) |
| *G01N 1/40* | (2006.01) |
| *G01N 21/64* | (2006.01) |
| *G16B 40/00* | (2019.01) |
| *G16B 45/00* | (2019.01) |
| *G16C 20/70* | (2019.01) |
| *G16C 20/80* | (2019.01) |
| *G16H 10/40* | (2018.01) |
| *G16H 20/10* | (2018.01) |
| *G16H 20/30* | (2018.01) |
| *G16H 30/40* | (2018.01) |
| *G16H 50/20* | (2018.01) |

(52) U.S. Cl.
CPC ............ *A61B 5/1455* (2013.01); *A61B 5/443* (2013.01); *A61B 5/444* (2013.01); *A61B 5/445* (2013.01); *A61B 5/4842* (2013.01); *A61B 5/7282* (2013.01); *G01N 1/405* (2013.01); *G01N 21/6428* (2013.01); *G01N 21/6456* (2013.01); *G16B 40/00* (2019.02); *G16B 45/00* (2019.02); *G16C 20/70* (2019.02); *G16C 20/80* (2019.02); *G16H 10/40* (2018.01); *G16H 20/10* (2018.01); *G16H 20/30* (2018.01); *G16H 30/40* (2018.01); *G16H 50/20* (2018.01); *A61B 5/4866* (2013.01); *A61B 2562/0233* (2013.01); *A61B 2576/02* (2013.01); *G01N 2021/6439* (2013.01)

(58) Field of Classification Search
CPC ....... A61B 5/444; A61B 5/445; A61B 5/4842; A61B 5/7282; A61B 5/4866; A61B 2562/0233; A61B 2576/02; G01N 1/405; G01N 21/6428; G01N 21/6456; G01N 2021/6439; G01N 21/255; G01N 21/6486; G16B 40/00; G16B 45/00; G16C 20/70; G16C 20/80; G16H 10/40; G16H 20/10; G16H 20/30; G16H 30/40; G16H 50/20; G16H 20/40; G16H 50/50

See application file for complete search history.

(56) References Cited

U.S. PATENT DOCUMENTS

| | | | | |
|---|---|---|---|---|
| 5,784,162 A | * | 7/1998 | Cabib | G01J 3/453 |
| | | | | 435/6.12 |
| 6,205,354 B1 | * | 3/2001 | Gellermann | A61B 5/443 |
| | | | | 356/301 |
| 6,998,247 B2 | * | 2/2006 | Monfre | G01N 21/359 |
| | | | | 435/14 |
| 8,025,851 B2 | | 9/2011 | Slowey et al. | |
| 8,385,615 B2 | * | 2/2013 | Levenson | G01N 21/6486 |
| | | | | 600/407 |
| 8,634,607 B2 | * | 1/2014 | Levenson | G01N 21/6456 |
| | | | | 600/475 |
| 10,146,912 B2 | | 12/2018 | Drysdale et al. | |
| 10,299,965 B1 | | 5/2019 | Brar | |
| 10,376,148 B2 | | 8/2019 | Wood et al. | |
| 10,438,356 B2 | * | 10/2019 | Dacosta | A61B 5/0071 |
| 10,517,483 B2 | | 12/2019 | Wood et al. | |
| 10,618,983 B2 | | 4/2020 | Mitragotri et al. | |
| 10,783,632 B2 | | 9/2020 | Fan et al. | |
| 2002/0016534 A1 | * | 2/2002 | Trepagnier | A61B 5/0062 |
| | | | | 600/316 |
| 2002/0082487 A1 | * | 6/2002 | Kollias | A61B 5/1455 |
| | | | | 600/316 |
| 2002/0091324 A1 | * | 7/2002 | Kollias | A61B 5/0071 |
| | | | | 600/476 |
| 2005/0131304 A1 | * | 6/2005 | Stamatas | G01N 21/64 |
| | | | | 600/476 |
| 2006/0092315 A1 | * | 5/2006 | Payonk | A61B 5/445 |
| | | | | 348/370 |
| 2007/0173725 A1 | | 7/2007 | Souta et al. | |
| 2007/0265532 A1 | * | 11/2007 | Maynard | A61B 5/14532 |
| | | | | 600/477 |
| 2007/0276199 A1 | * | 11/2007 | Ediger | A61B 5/0071 |
| | | | | 600/300 |
| 2008/0076985 A1 | * | 3/2008 | Matousek | A61B 5/0059 |
| | | | | 600/310 |
| 2008/0214460 A1 | | 9/2008 | Neuberger et al. | |
| 2009/0137908 A1 | * | 5/2009 | Patwardhan | A61B 5/444 |
| | | | | 600/476 |
| 2009/0162423 A1 | | 6/2009 | Neuberger et al. | |
| 2010/0168586 A1 | * | 7/2010 | Hillman | A61B 5/0075 |
| | | | | 348/E13.001 |
| 2011/0021973 A1 | | 1/2011 | Neuberger et al. | |
| 2011/0039342 A1 | | 2/2011 | Percival et al. | |
| 2012/0268573 A1 | * | 10/2012 | Schonborn | A61B 1/00009 |
| | | | | 348/E13.074 |
| 2013/0053677 A1 | | 2/2013 | Schoenfeld | |
| 2014/0163389 A1 | | 6/2014 | Kudenov et al. | |
| 2015/0287191 A1 | * | 10/2015 | Koruga | A61B 5/444 |
| | | | | 382/128 |
| 2016/0030132 A1 | | 2/2016 | Cheung et al. | |
| 2016/0166194 A1 | * | 6/2016 | Gareau | A61B 5/0075 |
| | | | | 600/328 |
| 2017/0160189 A1 | | 6/2017 | Priore | |
| 2018/0202927 A1 | | 6/2018 | Isikman et al. | |
| 2019/0133502 A1 | | 5/2019 | Gomi et al. | |

* cited by examiner

| | |
|---|---|
| TEMPERATURE | HIGH |
| PORPHYRIN | HIGH |
| VASCULATURE / BLOOD | LOW |
| COLLAGEN | LOW |
| CELLULAR ACTIVITY | HIGH |
| PH | HIGH |

FIG. 4

| SKIN FLUOROPHORE(S) BIOCHROMES | BIOMOLECULES / CELL LOCALIZATION | EXCITATION (NM) | EMISSION (NM) |
|---|---|---|---|
| AROMATIC AMINO ACIDS | PROTEINS PHE + TYR + TRP | 240 – 280 | 280 – 350 |
| COLLAGENS | EXTRAVASCULAR MATRIX (ECM) | 330 – 340 | 400 – 430 |
| ELASTIN | ECM + BLOOD VESSELS | 350, 420 | 420 / 525 |
| KERATINS | EPITHELIUM | 280, 325 | 495, 525 |
| REDUCED PYRIDINE NUCLEOTIDES | NADH / COFACTORS IN METABOLISM MITOCHONDRIA, CYTOPLASM | 330 – 380 | 440 (BOUND) 460 (FREE) |
| FLAVINS | RIBOFLAVIN, FMN, FAD | 350 – 370 | 480 – 540 |
| FLAVIN NUCLEOTIDES | CO-FACTORS / CO-ENZYMES | 440 – 450 | 480 – 540 |
| PORPHYRINS | PROSTHETIC GROUP OF PROTEINS | 405 – 500 | 630 / 670 |
| ZN-PROTOPORPHYRIN | HEMOGLOBIN | 405 – 600 | 630 / 670 |
| LIPOPIGMENTS | CELLULAR AGING | 400 – 500 | > 540 |
| VITAMINS | B6 | 290 – 310 | 400 – 500 |
| LIPIDS | ARACHIDONIC ACID | 330, 350 | 470 - 480 |

FIG. 10

| HEMOSTASIS AND CIRCULATION, RESIDENT CELLS | KEY PRODUCTS | TARGET CELL(S) FUNCTION |
|---|---|---|
| PLATELETS | FGF, TGF A/B, PDGF, VEGF, VWF, FGN, FN, PF4, ADP, ATP | KERATINOCYTE, EC, MACROPHAGE, FIBROBLAST (FB) |
| RBC | HBG, O2, O2, ATP, NO | PLATELET, EC |
| LANGERHANS CELL | MHC I, II | MICROBES, T CELLS |
| DENDRITIC CELL | TNF-α, IL 1β, INF-γ, NOS | MICROBES, T CELLS |
| KERATINOCYTE | KERATIN ECM/BM-COLLAGEN, VI, IV, LN, V, TGFβ, VEGF, CTGF, CYTOKINES, MMP1/TMP1 | PARACRINE/AUTOCRINE, ESC |
| ENDOTHELIAL CELL/SMC | GFS, MMPS, MTX/BM, GFRS/INTEGRINS/INOS + ENOS | EMC/EC, FB, ESC, MONOCYTE/MACROPHAGE/LYMPHOYTE ADHESION / EXTRAVASATION, FLOW + TONE (NOS/NO) |
| FIBROBLAST | MTX, MMP9/TIMP, CATHEPSIN, MTX (COLLAGEN/HYDROXYPROLINE/FN) TGFB, FGF, PDGF | EC, PERICYTE, MACROPHAGE |
| FERICYTE | TGFβ, VEGF, COLLAGENS | EC, TMX REMODELING, FLOW + TONE |

FIG. 11

| IMMUNE SURVEILLANCE CELLS | KEY PRODUCTS | TARGET CELL(S) |
|---|---|---|
| PMN | TNF-ALPHA, IL6,8, 1B, NFKB, IGG, MMP8, ELASTASE | MACROPHAGE, ENDOTHELIAL CELL, MICROBES |
| BASOPHIL | HEPARIN SP, LEUKOTRIENES, HISTAMINE | EC, MAST CELLS |
| MACROPHAGE M1/M2 | ROS, IL 1B, TNF-ALPHA, IL6/IL4, 10, 13, 21, TGFB, PGS | |
| T REGULATORY LYMPHOCYTE | TGFB, IL 10 | MACROPHAGE T/B CELLS |
| NATURAL KILLER CELL | INF-G, GMCSF | NEUTROPHIL |
| T HELPER LYMPHOCYTE | INF-G, TNF-A, ILS | B CELLS/CD40EXPRESSING, KERATINOCYTES, FB, MACROPHAGE, PLATELETS |

| | | |
|---|---|---|
| EPITHELIAL PROGENITOR/STEM CELL | VARIOUS GROWTH FACTORS | KERATINOCYTES |
| FOLLICULAR STEM CELL | GFS | KERATINOCYTES |
| ADIPOSE STEM CELL | GFS | MACROPHAGE, FB, EC, SMC |
| HEMATOPOIETIC SC/EPC | CYTOKINES, GFS | FB, MACROPHAGE/EC - ANGIOGENESIS |

FIG. 12

SKIN DIAGNOSTICS USING OPTICAL SIGNATURES

RELATED APPLICATIONS

This application claims the benefit of U.S. provisional patent applications "Systems and Methods for Wound Care Diagnostics and Treatment" Ser. No. 62/964,969, filed Jan. 23, 2020, and "Multispectral Sample Analysis Using Fluorescence Signatures" Ser. No. 63/132,541, filed Dec. 31, 2020.

Each of the foregoing applications is hereby incorporated by reference in its entirety.

FIELD OF ART

This application relates generally to skin diagnostics and more particularly to skin diagnostics using optical signatures.

BACKGROUND

Materials are all around us. We wear objects made from materials, live in structures constructed from materials, and travel in vehicles made from materials, to name only a very few uses of materials. A material is a substance or a mixture of substances that make up a given object. Examples of materials include wood, plastics, metals, fabrics, and glass. The materials that are commonly used include naturally occurring materials and synthetic materials. The materials can be used in their pure form or can be used in an "impure" or combined form. Here, an impure form of a material can include a compound, a composite, or a blend of materials. A material or combination of materials can usually be identified by studying various properties of the material in question. Material properties that are of particular interest include physical properties such as state, where material state includes solid, liquid, gas, or plasma states. Other physical properties include the density of the material and magnetic characteristics of the material. The material properties of interest further include chemical properties such as chemical resistance of the material to attack by other chemicals, and the combustibility of the material. The material properties can further include mechanical properties such as malleability, ductility, and strength; and electrical properties such as conductivity and resistivity. The properties of a material can also include optical properties such as transmissivity and absorptivity. Still other properties can also be used. Because each material has its own unique set of properties, the physical, chemical, mechanical, electrical, optical, and other responses of a material can be analyzed to characterize and identify unknown materials.

The analysis and characterization of materials has many applications in various industries including manufacturing, aerospace, and taxonomy, to name a few. The analysis and characterization of materials is also widely used in research applications to identify a material or materials within a sample, to characterize new alloys or compounds of materials, and so on. The analysis and characterization of materials can also be used to identify materials that should not be present within a sample. Some applications include identifying contaminants within materials, where the contaminants cause systems made from the materials to fail. Sophisticated tests and techniques can provide detailed information about a material, such as identifying its chemical composition. This latter class of analysis can require complex laboratory equipment and testing techniques. For example, a scanning electron microscope (SEM) uses a beam of electrons to reveal information about the surface topology and composition of a material, while a transmission electron microscope (TEM) can be used in crystalline defect analysis to predict behavior and to find failure mechanisms for materials. Also, X-ray Diffraction (XRD) is used to identify and characterize crystalline materials. These complicated and expensive tests, techniques, and types of equipment, usually available only in laboratories, can be used alone or in combination to characterize and identify unknown materials.

SUMMARY

Disclosed techniques can characterize and identify materials using one or more optical excitation light wavelength bands. Techniques for skin diagnostics using optical signatures disclosed herein use light from a range of wavelengths across the electromagnetic spectrum. The range of wavelengths corresponds to various types of light such as infrared (IR) light, long-wavelength IR (LWIR) light, visible light, and so on. The wavelengths can also include those that correspond to thermal energy. A light source excites electrons in molecules of a compound and causes the electrons to emit light, or fluoresce. Multispectral images are captured with a broad-spectrum imaging sensor and low-cost optical filtering techniques, such as a color gel or dielectric filter. The broad-spectrum imaging sensor provides sensitivities to particular wavelengths, including light frequencies which are visible to the human eye, and light frequencies which are not (e.g., IR, thermal). Materials reflect and absorb light differently at different wavelengths. Thus skin diagnostics using optical signatures can be used to differentiate materials based on their spectral signatures, including their fluorescence characteristics, their light reflection characteristics, their light absorption characteristics, and even their light transmission characteristics.

Disclosed techniques address a method for skin diagnostics using optical signatures. The disclosed techniques enable handheld, portable, multispectral material sample analysis. A plurality of optical excitation light wavelength bands is scanned on a material sample. The material sample that is scanned exhibits optical spectral characteristics along the light wavelength spectrum. The optical excitation light wavelength bands and the exhibited optical spectral characteristics of the material sample can include IR light, long-wavelength IR light, visible light such as Red-Green-Blue (RGB) light, fluorescent light, and so on. The material sample can include cells, tissues, and organs. The material sample can be from a wound. Excitation response wavelengths emitted by the material sample are captured in response to the plurality of optical excitation light wavelength bands. The capturing is accomplished using an imaging sensor such as an IR sensor, a thermal sensor, an RGB sensor, and the like. Output values of a plurality of pixels of an image from the imaging sensor are measured. The output values can be represented by analog or digital signals. The image from which pixel values are measured represents excitation response wavelengths captured by the imaging sensor. The measuring detects optical spectral characteristics of the material sample, and the optical spectral characteristics are in response to the plurality of optical excitation light wavelength bands. The plurality of optical excitation light wavelength bands can include one or more non-fluorescent optical excitation light wavelength bands, where more non-fluorescent optical excitation light wavelength bands coincide with one or more absorption wavelength maximums of selected material constituents. An output signature that is indicative of composition of the material sample is generated. The output signature is based on interpreting the output values that were measured. The output signature can be indicative of the presence of nicotinamide adenine dinucleotide plus hydrogen (NADH) and flavins, the presence of collagen, the presence of porphyrins, the presence of infection, etc. The output signature can be regenerated over time. The regenerating the output signature over time informs a wound care treatment plan.

A method for skin diagnostics is disclosed comprising: scanning a plurality of optical excitation light wavelength bands on a material sample, wherein the material sample exhibits optical spectral characteristics along the light wavelength spectrum; capturing excitation response wavelengths emitted by the material sample in response to the plurality of optical excitation light wavelength bands, wherein the capturing is accomplished using an imaging sensor; measuring output values of a plurality of pixels of an image from the imaging sensor, wherein the image represents excitation response wavelengths captured by the imaging sensor, wherein the measuring detects optical spectral characteristics of the material sample, and wherein the optical spectral characteristics are in response to the plurality of optical excitation light wavelength bands; and generating an output signature indicative of composition of the material sample, wherein the output signature is based on interpreting the output values that were measured.

Various features, aspects, and advantages of various embodiments will become more apparent from the following further description.

BRIEF DESCRIPTION OF THE DRAWINGS

The following detailed description of certain embodiments may be understood by reference to the following figures wherein:

FIG. 4 is a table for identifying infection.

FIG. 10 is a table showing biochromes and fluorescent channels.

FIG. 11 is a table showing cells associated with hemostasis and wound healing.

FIG. 12 is a table showing immune surveillance cells.

DETAILED DESCRIPTION

Figure 1:
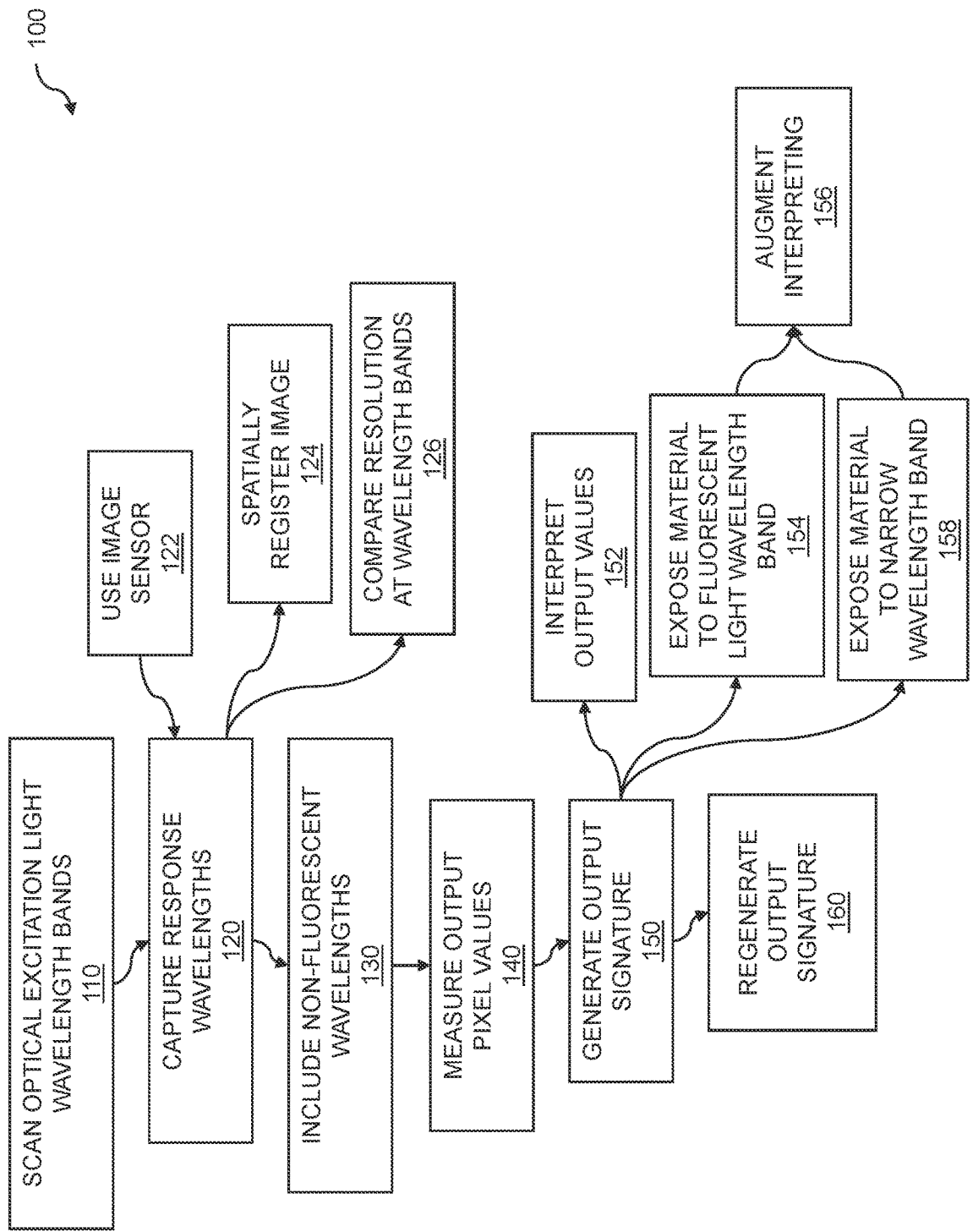
FIG. 1 is a flow diagram for skin diagnostics using optical signatures.

Techniques for skin diagnostics based on optical signatures are disclosed. At least one optical excitation light wavelength band is scanned on a material sample, where the material sample can include cells, tissues, or organs. Excitation response wavelengths that are emitted by the material sample are captured in response to the optical excitation light wavelength bands used to scan the material sample. The response wavelengths are captured using an imaging sensor. Output values of pixels of an image from the imaging sensor are measured. An output signature that is indicative of composition of the material sample is generated. The output signature is based on interpreting the output values that were measured. The output signature enables wound care management and provides a wound healing trajectory. The output signature is generated over time and enables a would care treatment plan.

Fluorophores with different emission spectra can be distinguished based on comparison of their infrared (IR), Red-Green-Blue (RGB), and long-wavelength IR (LWIR) emission signals. A fluorescence signal can be spectrally resolved using filters common to many digital imagers. The digital imagers can include color digital imagers such as the Red, Green, and Blue color gels used in Bayer patterned sensors, IR imagers, thermal imagers, and so on. The imagers can be integrated in typical, inexpensive sensors such as RGB sensors that are the basis of common color digital imagers. These sensors generally demonstrate peak blue sensitivity at 400-475 nm, peak green sensitivity at 475-580 nm, and peak red sensitivity at 580-750 nm. One or more optical excitation sources can be provided to provide the excitation light wavelength bands. In a usage example, an optical excitation source at a wavelength is provided near the edge of, or slightly inside or outside of, the RGB visible light wavelength spectrum, such as at 405 nm. However, it should be noted that the definition of the exact wavelengths of visible light is somewhat subjective. For purposes of discussion, a visible light wavelength range of about 425 nm to about 725 nm is understood herein, although discrete wavelengths or wavelength ranges are used when possible. The optical excitation source wavelength can, when used to illumine a material sample, elicit a fluorescence response from the material sample that can be detected by a sensor such as an RGB sensor, a thermal sensor, an IR sensor, and so on. In order to prevent crosstalk from the excitation source into the spectral channels detected by the one or more imagers, the excitation source may be outfitted with a bandpass filter. This technique can be especially useful if the excitation source exhibits a long "red-side" tail into the longer wavelengths detectable by the RGB or other sensor. Additionally, a long-pass filter placed in front of the sensor can prevent spurious signals from the excitation source, such as an LED, from reaching the sensor.

The low-cost, portable method of skin diagnostics using optical signatures disclosed herein can use an ordinary, readily available, Red-Green-Blue (RGB) sensor. The RGB sensor typically is mass produced and has applications in low-cost technology that endeavors to detect light waves in the visible spectrum in a standard three-color, RGB palette suitable for digital processing. Other low-cost sensors can include IR sensors, thermal sensors, and so on. The RGB sensor typically employs an integrated Bayer filter applied during the manufacturing process of a Complementary Metal Oxide Semiconductor (CMOS), Charged Coupled Device (CCD), or similar sensor semiconductor fabrication. The Bayer filter is completely integrated into the sensor and cannot be removed, replaced, or adjusted. When light impinges the surface of an RGB sensor, the underlying photosensors register a signal related to the intensity of the impinging wavelengths as a function of the color of the integrated sensor directly over each photosensor device. The disclosed technology does not require expensive filter wheels, complex optical alignments, or stationary, non-handheld components.

FIG. 1 is a flow diagram for skin diagnostics using optical signatures. Optical excitation light wavelength bands are scanned on a material sample. The material sample exhibits optical spectral characteristics along the light wavelength spectrum. Excitation response wavelengths are captured, where the excitation response wavelengths are emitted by the material sample in response to optical excitation light wavelength bands. The capturing is accomplished using an imaging sensor. Output values of pixels of an image from the imaging sensor are measured. An output signature is generated, where the output signature is indicative of the composition of the material sample.

The flow 100 includes scanning a plurality of optical excitation light wavelength bands 110 on a material sample. The material sample can include a solid, a liquid, a gel, and so on. In embodiments, the material sample can include cells, tissues, and organs. The material sample can include healthy cells, tissues, and organs, or damaged cells, tissues, and organs. In embodiments, the material sample can be from a wound. The material sample that is scanned exhibits optical spectral characteristics along the light wavelength spectrum. The optical spectral characteristics that are exhibited can include fluorescence characteristics. The fluorescence characteristics can occur at the same wavelength as the excitation light or at a different wavelength. The scanned material can exhibit other optical qualities. In embodiments, the plurality of optical excitation light wavelength bands can include one or more non-fluorescent optical excitation light wavelength bands. Based on the type of material that is scanned, the one or more non-fluorescent optical excitation light wavelength bands can coincide with one or more absorption wavelength maximums of selected material constituents (discussed below).

The optical excitation light wavelength bands can include infrared (IR) bands, visible light bands (e.g., red-green-blue, or RGB), long-wavelength IR (LWIR) bands, thermal bands, and so on. In embodiments, a first band of the plurality of optical excitation light wavelength bands can include wavelengths substantially in the range of 325 nm to 375 nm, a second band of the plurality of optical excitation light wavelength bands can include wavelengths substantially in the range of 350 nm to 400 nm, and a third band of the plurality of optical excitation light wavelength bands can include wavelengths substantially in the range of 375 nm to 425 nm. Other bands can also be used. In other embodiments, a fourth band of the plurality of optical excitation light wavelength bands comprises wavelengths substantially in the range of 400 nm to 450 nm. The optical excitation light wavelength bands can include wide bands or narrow bands. In embodiments, the plurality of optical excitation light wavelength bands can include narrow bands substantially at 350 nm, 375 nm, 400 nm, 425 nm, 450 nm, 500 nm, 525 nm, 550 nm, 575 nm, 600 nm, 625 nm, and so on.

The flow 100 includes capturing excitation response wavelengths 120 emitted by the material sample in response to the plurality of optical excitation light wavelength bands. The excitation response wavelengths can include one or more wavelengths. In the flow 100, the capturing is accomplished using an imaging sensor 122. The imaging sensor can include an IR sensor, a thermal sensor, and so on. In embodiments, the sensor can include an RGB sensor. The sensor can produce analog or digital output signals. The output values of a sensor, such as an RGB sensor, can include electrical signals, and thus the RGB sensor translates wavelength intensity to an electrical representation by providing three output values: a red output value, a green output value, and a blue output value. These sensors generally demonstrate peak blue sensitivity at 400-475 nm, peak green sensitivity at 475-580 nm, and peak red sensitivity at 580-750 nm. In order to avoid signal contribution from an excitation LED (or other excitation source) that has a long red tail that may be detected by the spectral channels built into the RGB imager, the excitation source may be outfitted with a bandpass filter that prevents crosstalk. Additionally, a long-pass filter placed in front of the RGB sensor further prevents a spurious signal from the excitation LED. The flow 100 further includes spatially registering the image 124 to determine wound features contained in the material sample. In a usage example, the spatially registering the image can include locating a wound, locating a wound edge, locating a wound center, and so on. The flow 100 further includes comparing image resolution 126 at a plurality of narrow optical excitation light wavelength bands. The comparing image resolution at narrow wavelength bands can provide further information associated with the material sample such as a wound sample. In embodiments, the comparing can enable wound depth analysis.

In the flow 100, the plurality of optical excitation light wavelength bands can include one or more non-fluorescent 130 optical excitation light wavelength bands. When scanning a material to determine its constituents, a "negative response" such as a non-fluorescent response can provide useful clues associated with the material. In embodiments, the one or more non-fluorescent optical excitation light wavelength bands can coincide with one or more absorption wavelength maximums of selected material constituents. The flow 100 includes measuring output values 140 of a plurality of pixels of an image from the imaging sensor. The measuring output values can be based on measuring fluorescence, measuring absorption, and so on. The image from which pixels are measured can represent excitation response wavelengths captured by the imaging sensor. Further, the measuring output values can include measurements at the absorption wavelength maximums. The measuring detects optical spectral characteristics of the material sample that was scanned. The optical spectral characteristics are measured in response to the plurality of optical excitation light wavelength bands. The measurements can occur at fluorescent wavelengths, absorption wavelengths, and so on. In embodiments, the measurements at the absorption wavelength maximums augment interpreting (discussed below).

The flow 100 includes generating an output signature 150 indicative of composition of the material sample. The output signature can include a variety of indicators and markers. The signature can be based on numerical values, a range of values, ratios, percentages, qualitative evaluations, and so on. In embodiments, the output signature of the wound can include microbe indications, inflammation markers, granulation markers, epithelialization markers, and remodeling markers. The output signature can enable wound care management, where wound care management can include various treatments associated with the wound. In embodiments, the output signature provides a wound state or a wound healing trajectory. The wound state can include a stalled state, a healing state, a non-healing state, an infected state, an inflamed state, a granulating state, or an epithelializing state. The output signature can be indicative of the presence or absence of various constituents within the material sample. In embodiments, the output signature can be indicative of the presence of nicotinamide adenine dinucleotide plus hydrogen (NADH) and flavins. In other embodiments, the output signature can be indicative of the presence of collagen. The NADH, flavins, and collagen can be critical to wound healing. In the flow 100, the output signature is based on interpreting 152 the output values that were measured. The interpreting can be based on output values from the imaging sensor, and the output values can be indicative of one or more wavelengths. In embodiments, the interpreting can be based on measured wavelengths substantially in the range of 440 nm to 500 nm and 500 nm to 550 nm. Other light wavelengths can also be used. The flow 100 further includes exposing the material sample to a fluorescence excitation light 154 wavelength band. The fluorescence excitation light wavelength band comprises wavelengths substantially in the 315 nm to 375 nm range. In the flow 100, the exposing the material to the fluorescence excitation light wavelength band augments 156 the interpreting. The fluorescence excitation light wavelength band can cause further fluorescence of the material. Note also that the measurements at the absorption wavelength maximums (discussed above) can augment the interpreting. In other embodiments, the interpreting can be based on measured wavelengths substantially in the range of 600 nm to 660 nm and 675 nm to 725 nm. The flow 100 further includes exposing the material sample to a narrow fluorescence excitation light wavelength band 158 comprising wavelengths substantially at 400 nm to augment the interpreting 156.

The flow 100 includes regenerating the output signature 160 over time. The regenerating the output signature can be performed based on updated parameter values associated with a wound, changes in fluorescence response, changes in absorption response, and the like. The regenerating the output signature over time can be used to determine whether a wound is healing properly, is healing slowly, is not healing, and so on. In embodiments, the regenerating the output signature over time can inform a wound care treatment plan. The wound care treatment plan can include therapies including medicinal therapies, surgery, and so on.

Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors.

Figure 2:
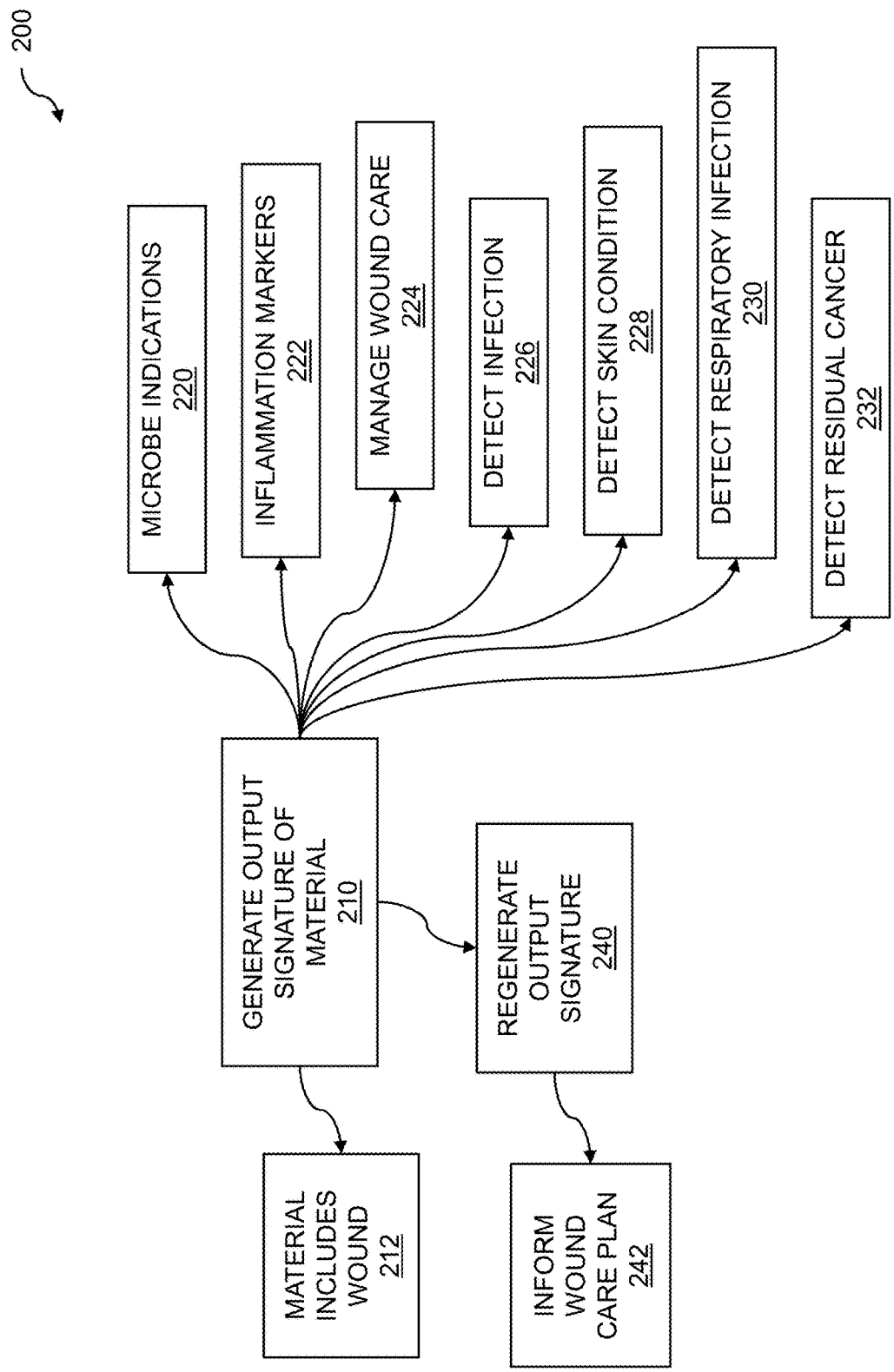
FIG. 2 is a flow diagram for output signature usage.

FIG. 2 is a flow diagram for output signature usage. An output signature that is associated with a material sample can be generated based on measured excitation responses. The measured excitation responses are based on captured excitation response wavelengths that result from scanning a material sample with various light wavelength bands. Output signature usage is enabled by skin diagnostics using optical signatures. A plurality of optical excitation light wavelength bands is scanned on a material sample. The material sample can include cells, tissues, and organs. Excitation response wavelengths emitted by the material sample are captured in response to the plurality of optical excitation light wavelength band. Output values are measured of a plurality of pixels of an image from the imaging sensor, and an output signature indicative of composition of the material sample is generated.

The flow 200 includes generating an output signature 210 indicative of composition of the material sample, wherein the output signature is based on interpreting the output values that were measured. The measuring can be based on capturing excitation response wavelengths emitted by the material sample in response to the plurality of optical excitation light wavelength bands. In embodiments, the output signature can describe one or more of temperature, granulation, NADH, water, vascularization, and tissue oxidation. The output signature can indicate the presence of biochemical species such as cells, enzymes, proteins, mediators, chemokines, cytokines, growth factors, proteases, inhibitors, receptors, and so on, as well as healing stages such as hemostasis, infected, inflamed, granulating, epithelializing, remodeling, and so on. The optical excitation light wavelength bands can include a first band of the plurality of optical excitation light wavelength bands comprising wavelengths substantially in the range of 325 nm to 375 nm, a second band of the plurality of optical excitation light wavelength bands comprising wavelengths substantially in the range of 350 nm to 400 nm, and a third band of the plurality of optical excitation light wavelength bands comprising wavelengths substantially in the range of 375 nm to 425 nm. Other optical excitation light wavelength bands may also be used. Various material samples can be scanned by the optical excitation light wavelength bands. The material sample can include cells, tissues, and organs. The material sample can include a biopsy sample, a liquid such as exudate, and so on. In the flow 200, the material sample is from a wound 212.

The output signature can include one or more of indications, markers, and so on, associated with a wound. In the flow 200, the output signature of the wound includes microbe indications 220. The microbe detection can be used to confirm the presence of an infection and the type of infection. Knowing the species of microbes present in a wound can be used to determine treatment. In the flow 200, the output signature of the wound includes inflammation markers 222. The inflammation markers can detect swelling, elevated temperature, the presence of red lines emanating from the wound, etc. The output signature of the wound further includes granulation markers, epithelialization markers, and remodeling markers. One or more of these markers can be used to characterize a wound, gauge wound healing, and so on. In the flow 200, the output signature enables wound care management 224. The wound care management can include treatment techniques including drug therapies. The drug therapies can include antibiotics to combat microbes, immunosuppression to quell autoimmune conditions, etc. In embodiments, the output signature can provide a wound healing trajectory.

In the flow 200, the output signature enables infection detection 226. Discussed throughout, some wounds can include stalled-healing or nonhealing wounds. These stalled-healing and nonhealing wounds can result from wound parameter imbalances, lack of proteins, and the like. In embodiments, the infection detection can be based on biochrome identification. The biochrome identification can be used to measure parameters associated with a wound, to identify microbes associated with an infection, and so on. In the flow 200, the output signature is used to detect one or more skin conditions 228. Various types of skin conditions can be detected. In embodiments, the skin conditions can include chronic wounds, radiation burns, acne, hives, eczema, psoriasis, cold sores, rosacea, thermal burns, and so on. In the flow 200, the output signature is used to detect respiratory infection 230. A respiratory infection can be associated with the common cold, tonsillitis, laryngitis, sinus infection, and so on. In embodiments, the respiratory infection detection can include influenza detection. Other respiratory infections can be detected. In embodiments, the respiratory infection detection can include COVID-19 detection. In the flow 200, the output signature is used to enable residual cancer detection 232. The residual cancer detection can be performed during surgery, treatment, and so on. In embodiments, the residual cancer detection can occur during oncological surgery. In addition to using the output signature to evaluate chronic wounds or skin conditions, the output signature can be used to evaluate skin cancer.

The flow 200 includes regenerating the output signature 240 over time. The output signature can be regenerated for a variety of purposes such as gauging the depth and extent of a wound, changing the parameter values associated with the wound, and so on. In the flow 200, the regenerating the output signature over time can inform a wound care treatment plan 242. The treatment plan can include a care of the wound such as cleaning and rebandaging the wound, a drug therapy, and so on. In a signature usage example, a wound can be cleaned and redressed daily while a patient is provided with intravenous antibiotics. As the patient heals, the intravenous antibiotics can be replaced by oral antibiotics and the frequency of dressing changes can be reduced. Further, if the regenerating the output signature indicates that the wound is not healing at a sufficient rate, then the treatment protocols for the wound can be adapted, changed, etc.

Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors.

The wound healing process is complex. There are in excess of 13 critical parameters local to the wound that control the healing process, and if not at correct levels can stall healing indefinitely. These parameters include but are not limited to: collagens, glucan, IL1β, IL6, TNF, pH, MMP1, MMP2, MMP8, MMP9, MMP13, TGFβ1, Angiopoietin-1, Angiopoietin-2, Angiogenin, endostatin, CD105, CD31, GM-CSF, TIMP1-4, hyaluronic acid, Collagens I/III/IV, IL10, VEGF, HB-EGF, EGF, PDGF, fibroblasts, water, hyaluronic acid, interleukins, angiogenesis factors, porphyrins, pyoverdines, lipofuscin, and metabolic factors such as NADH and FAD. Because the process is dynamic, these parameters change over time. In addition, the wound is not homogenous, and the parameters vary by location, as well.

Wounds will not heal properly or at all if there is an infection. In general, infections are caused by microbes that can populate the wound and grow at an exponential rate. While these microbes are present to some degree in all wounds and skin surfaces, they are harmful to wound healing when they reach such a critical population and virulence that they begin to induce injury in the host. That is, infection is not just the presence of bacteria, but also the presence of a host response and injury. It is this inflammatory response that can interrupt the native healing process, allow further propagation of the microbe or pathogen, and result in deterioration of the wound to an acute or chronic state. This deterioration process can cascade, with the initial infection allowing the wound to decline to a point where additional microbes can contaminate, colonize, and infect the wound. As a result, the compromised wound is trapped in a state of chronic nonhealing or further deterioration. Currently, there is no clinical technique for determining the presence, abundance and/or location of infecting microbes and resulting host inflammatory responses. Technology that could identify the site of infection and inflammation and help assess the presence or absence of infecting microbes would satisfy an unmet need in clinical settings.

Host responses such as those which are seen with infection can also be caused by autoimmune disorders (no infecting microbes) such as pyoderma gangrenosum. Pyoderma gangrenosum is thought to be an immune response injury and the treatment (immune suppression) is different from microbial infections, and therefore requires careful diagnosis. Once the infection has been identified and treated, over 50% of all chronic wounds still do not heal, even when there is no infection. This is because one or more of the critical wound parameters or vital signs is not in the correct range. Disruptions to the wound healing process may be related to excess or lack of biochemical species. For example, fibroblasts may be producing collagen, only for it to be destroyed by an excess of collagenase created by another cell or biochemical process, resulting in stalled healing. A precise balance of cells, extra-cellular matrix, and biochemicals are necessary for wound healing. Accurately measuring the relative abundance of these components can call for targeted treatments to repair the underlying healing mechanisms.

Figure 3:
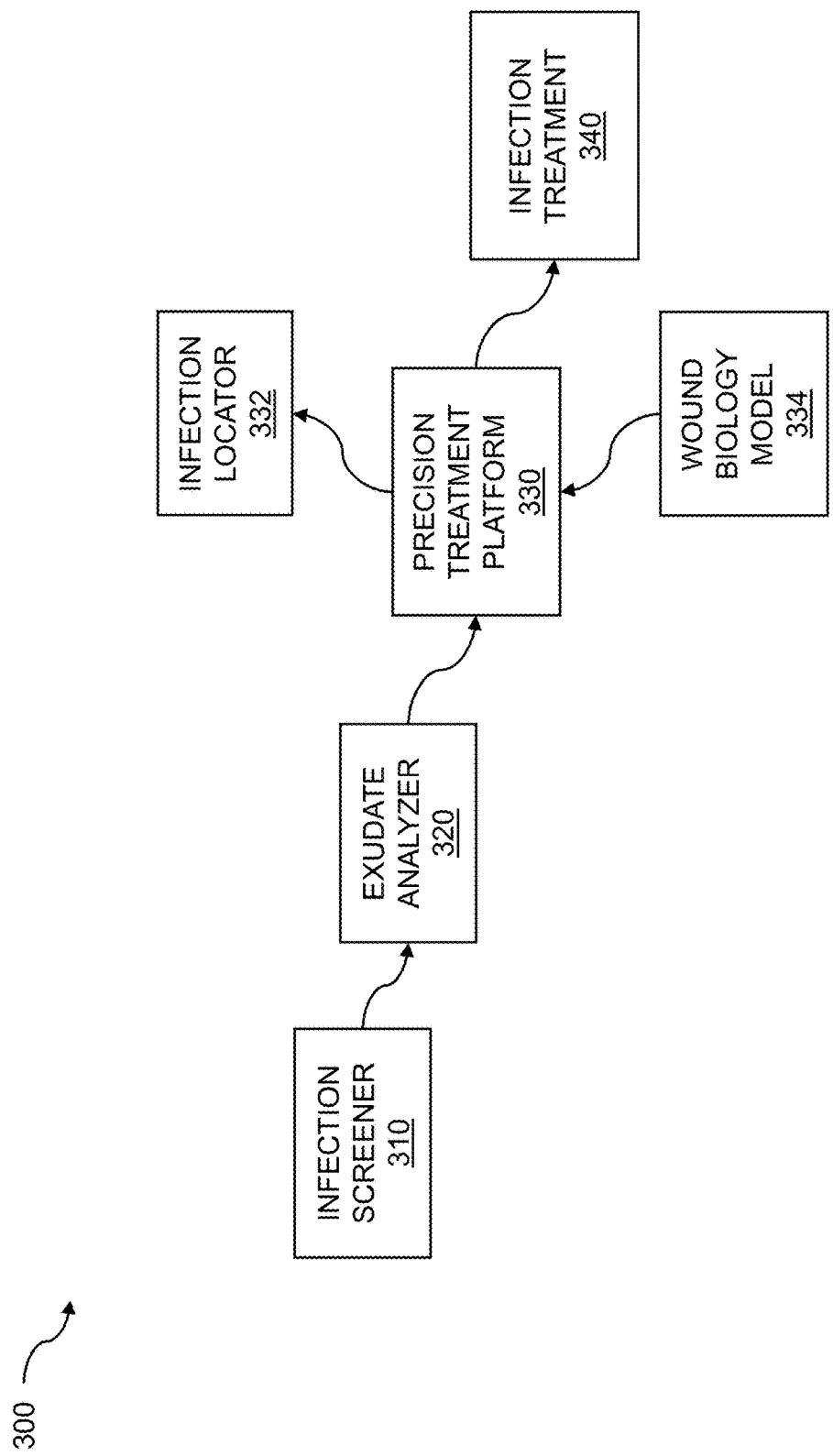
FIG. 3 shows a system block diagram for diagnosis and treatment.

FIG. 3 shows a system block diagram for diagnosis and treatment. Discussed throughout, optical signatures can be generated based on scanning one or more light wavelength bands on a material sample such as a skin sample. The skin diagnostics can include determining a wound location, identifying infection, determining healing progress, and so on. Using optical signatures enables skin diagnostics. A plurality of optical excitation light wavelength bands is scanned on a material sample, where the material sample exhibits optical spectral characteristics along the light wavelength spectrum. Excitation response wavelengths emitted by the material sample in response to the plurality of optical excitation light wavelength bands are captured, where the capturing is accomplished using an imaging sensor. Output values of a plurality of pixels of an image from the imaging sensor are measured, where the image represents excitation response wavelengths captured by the imaging sensor, where the measuring detects optical spectral characteristics of the material sample, and where the optical spectral characteristics are in response to the plurality of optical excitation light wavelength bands. An output signature indicative of composition of the material sample is generated, where the output signature is based on interpreting the output values that were measured.

Precision medicine techniques for skin diagnostics can be used to identify whether one or more critical parameters such as wound parameters are within ranges which enable healing or not. The one or more wound parameters are associated with the skin diagnostics. Based on the assessed parameters, one or more treatments can be recommended that address results of diagnostics such as wound locating, wound treatment, treatment efficacy, and so on. The system block diagram 300 includes an infection screener 310. The infection screener can include an imaging component which can be used to locate infection. The infection can include a skin infection, a respiratory infection, residual cancer, and so on. In embodiments, the infection can include a COVID-19 infection. The system block diagram 300 can include an assay component such as an exudate analyzer 320. The assay component can include a lab-based component, a bedside component, and so on. In the block diagram 300, data associated with the infection screener and data associated with the exudate analyzer can be provided to a precision treatment platform 330. The precision treatment platform can use the imaging data from the infection screener to perform infection location 332. The infection location can be associated with skin, sinuses, or lungs; a wound; and the like. The precision treatment platform can use the exudate analysis data to generate a wound biology model 334. Based on the infection location and the wound biology model, an infection treatment component 340 can be used to propose infection treatment. The proposed infection treatment can be presented as an array (described below). The infection treatment component can rank treatments to determine a most appropriate treatment for an individual patient.

Infection location can be accomplished non-invasively using a combination of fluorescence and reflectance images generated at specific excitation and emission wavelengths. Cellular and molecular species exist in the wound and peri-wound areas. The fluorescence and reflectance images can exhibit spectral signatures, where the spectral signatures can be compared to known spectral signatures. The spectral signatures can be extracted, calculated, and analyzed, and can be used to identify signatures including infection signatures, healing signatures, nonhealing signatures, and the like. A variety of techniques can be used for locating infection, whether the infection is associated with a wound, a respiratory infection, a COVID-19 infection, residual cancer detection, and so on. Discussed above and throughout, infection detection can be accomplished using a handheld device, a cart-based device, etc. The detection can be based on fluorescence measurements, absorption measurements, reflection measurements, and/or transmission measurements, or any combination of measurements thereof. The detection can further be based on absorption and reflection of various excitation light wavelength bands by tissue such as wound tissue, and it can be augmented by fluorescence measurements.

With regard to wound healing measurements, it is important to note that about half of chronic wounds are not infected. These wounds are chronic and slow healing due to an imbalance of healing factors, mostly related to poor blood supply and elevated protease activity, which destroys needed proteinaceous signals required for healing. There are numerous treatments that attempt to address this, but there can be ten to twenty factors that work together to foster healing. Further, no single treatment addresses all of them. Key wound factors, signaling pathways, and immigrant and resident dermal cells coordinating reparative and regenerative responses post-injury are discussed below. The imager can assess a number of key biomarkers, but additional analysis may be necessary to fully assess a wound. The analysis can require extraction and assessment of wound exudate.

FIG. 4 is a table for identifying infection. Identifying that an infection is present, and determining the type of infection, can be critical to treating the infection, promoting healing of a wound, and so on. Identifying infection enables skin diagnostics, where the skin diagnostics are based on optical signatures. A plurality of optical excitation light wavelength bands is scanned on a material sample, where the material sample exhibits optical spectral characteristics along the light wavelength spectrum. Output values of a plurality of pixels of an image from the imaging sensor are captured, where the image represents excitation response wavelengths captured by the imaging sensor, where the measuring detects optical spectral characteristics of the material sample, and where the optical spectral characteristics are in response to the plurality of optical excitation light wavelength bands. An output signature indicative of composition of the material sample is generated, where the output signature is based on interpreting the output values that were measured.

Table 400 shows example wound parameters that can be determined based on scanning a material sample such as a skin sample using a plurality of optical excitation light wavelength bands. The table can include one or more parameters 410 and values 412 associated with the one or more parameters. The parameters can include temperature, porphyrin, vasculature/blood flow, collagen, cellular activity, pH, and so on. The values associated with the one or more parameters can include a numerical value, a range of values, a percentage, a quality, an assessment, and so on. Table 400 shows qualitative values or assessments assigned to the one or more parameters. Based on the optical excitation light wavelength scans of the skin sample, infection can be determined from high temperature, high porphyrin, low vasculature/blood flow, low collagen, high cellular activity, high pH, etc.

Figure 5:
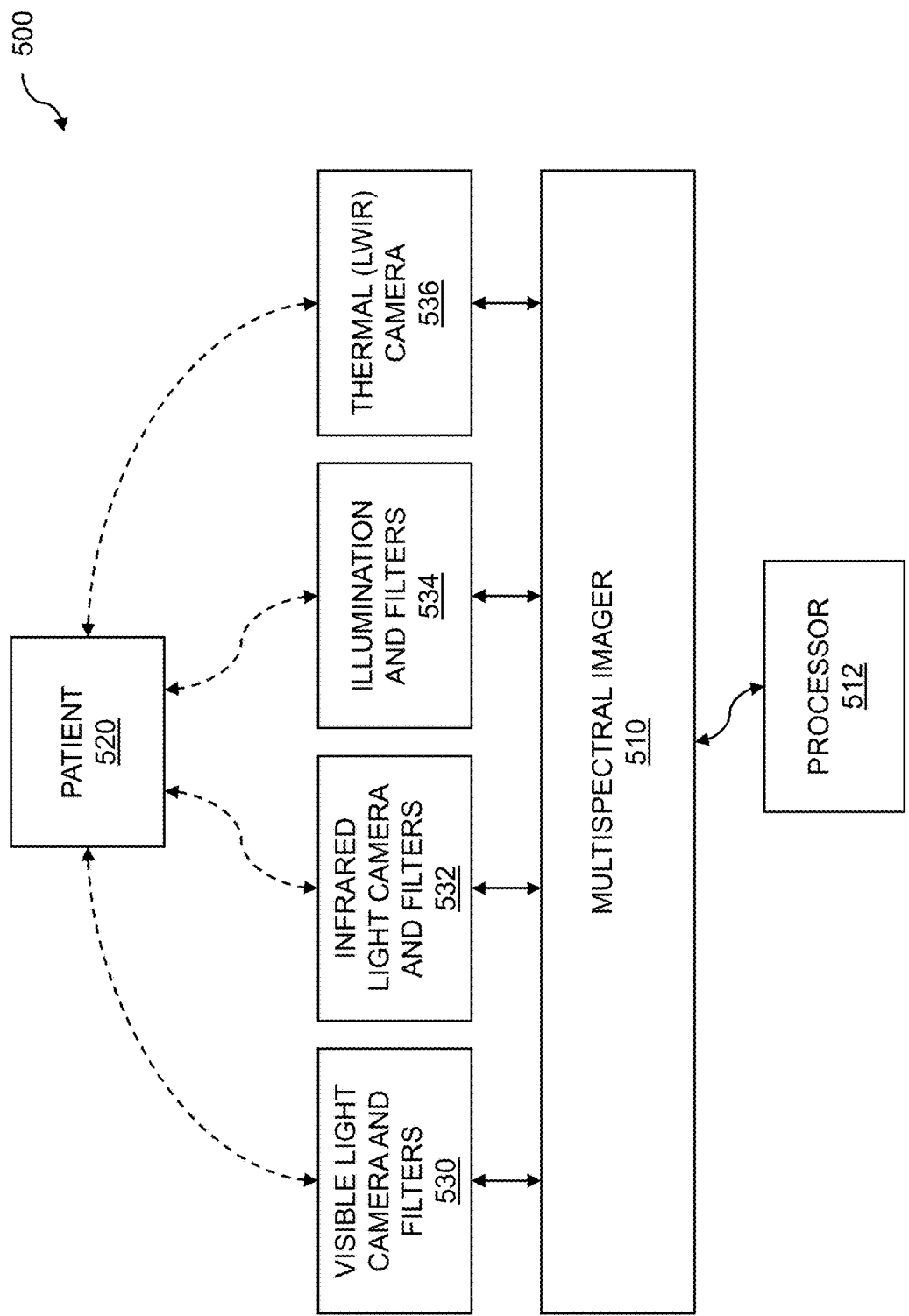
FIG. 5 is a system block diagram for infection locating.

FIG. 5 is a system block diagram for infection locating. A patient can present with one or more indications that can be associated with an infection. Locating the infection can be critical to providing appropriate care to the patient to help her recover from the infection. Locating an infection can be associated with locating a wound or other damage to the skin of the patient. Other infections, such as respiratory infections and COVID-19 infections, and detection of residual cancer, among others, can be harder to locate or identify because the infections or residual cancer are likely not visible. In these and other cases, optical techniques may be applied to infection locating. The infection locating enables skin diagnostics using optical signatures. Optical excitation light wavelength bands are scanned on a material sample. The material sample exhibits optical spectral characteristics along the light wavelength spectrum. Excitation response wavelengths emitted by the material sample in response to the optical excitation light wavelength bands are captured using an imaging sensor. Output values of a plurality of pixels of an image from the imaging sensor are measured. The image represents excitation response wavelengths captured by the imaging sensor. An output signature indicative of composition of the material sample is generated. The output signature is based on interpreting the output values that were measured.

The system block diagram 500 includes a hyperspectral or multispectral imager 510. The multispectral imager can be based on a handheld component, a mobile cart-based component, and so on. The multispectral imager can receive data from one or more cameras (discussed below) and can measure fluorescence, absorption, and reflection of wound tissue at a variety of optical excitation light wavelength bands. The multispectral imager can be coupled to a processor 512. The processor can control illumination sources, filters, cameras, sensors, and so on. The processor or processors can execute code, where the code can perform various operations associated with the infection detection. The code can include code for control, image processing, data analysis, etc. The processor can be used to isolate signals from biochromes associated with infection. The signal isolation from biochromes associated with infection can be accomplished by scanning a material sample with one or more optical excitation light wavelength bands. The excitation wavelength can be held constant while one or more signals are collected from progressively longer wavelength emission bands. In embodiments, the multispectral imager can collect and isolate signals associated with nicotinamide adenine dinucleotide plus hydrogen (NADH) and flavins by collecting 440-500 and 500-550 nm emission photons, respectively, and scanning excitation (325-375 nm, 350-400 nm, 375-425 nm, 400-450 nm).

The multispectral imager can be used to locate infection associated with a patient 520. The infection can include an infection associated with a material sample such as skin, a respiratory infection, a particular infection such as a COVID-19 infection, residual cancer detection, and so on. The infection location can be accomplished using a handheld scanner, a cart-based scanner, and the like, as discussed throughout. The multispectral imager can be coupled to a variety of components including illumination sources, filters, cameras, and so on. The system block diagram 500 includes a visible light camera and filters 530. The camera can include an imaging sensor, where the imaging sensor can detect wavelengths within the visible light band. The visible light band can include one or more wavelengths between 380 nm and 700 nm. The visible light filters can include one or more of a red filter, a green filter, a blue filter, etc. The system block diagram 500 includes an infrared light camera and filters 532. The infrared camera, which can be based on an infrared imaging sensor, can detect wavelengths within the infrared band. The infrared band can include wavelengths between 780 nm and 1 mm. The infrared filters can be used to capture or isolate one or more wavelength bands within the infrared band. The system block diagram 500 can include illumination and filters 534. The illumination can be based on a plurality of optical excitation light wavelength bands, where the light wavelength bands can include visible light, IR light, long wavelength infrared (LWIR) light, and so on. The filters can include one or more filters which can be used to provide specific optical excitation light wavelengths. The system block diagram 500 can include a thermal (LWIR) camera 536. As noted throughout, detection of infection can include detection of elevated temperature or a "hot spot" on a material sample such as a skin sample. In the system block diagram 500, the illumination and filters can be used to provide a plurality of optical excitation light wavelength bands that can be scanned on a material sample. The material sample, such as a skin sample, a body part, a limb, exudate, and so on, can be associated with the patient 520.

Figure 6:
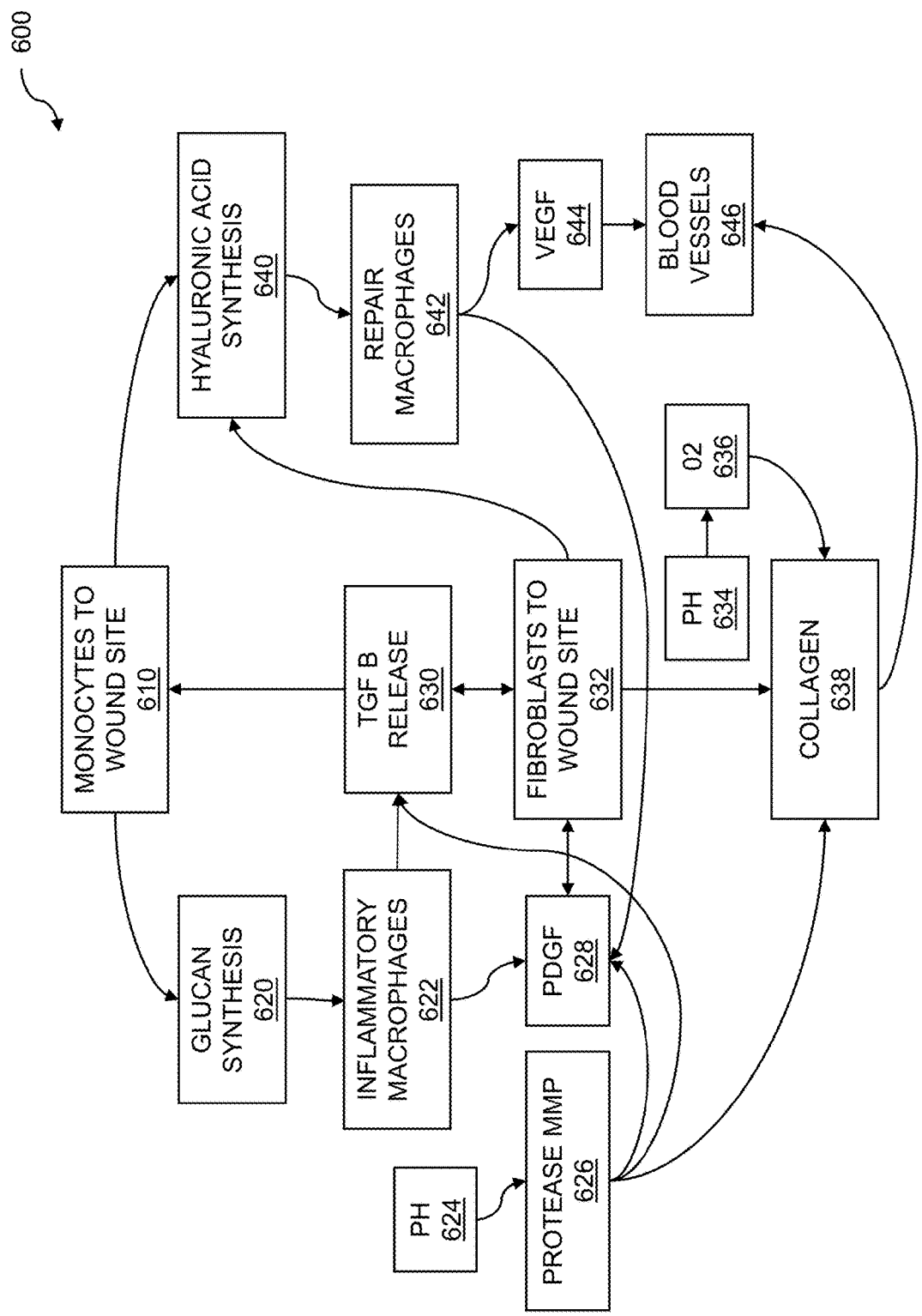
FIG. 6 is a system block diagram for dermis healing.

FIG. 6 is a system block diagram for dermis healing. A dermis healing assessment can be based on performing wound healing measurements, where the wound healing measurements can be based on exudate analysis. While some chronic wounds may not be infected, they can remain chronic or can be slow to heal. The slow healing can be due to a variety of factors such as poor blood supply, elevated protease activity, and so on. The latter can destroy proteinaceous signals that are required for healing. The dermis healing can be improved by skin diagnostics using optical signatures. Optical excitation light wavelength bands are scanned on a material sample. Excitation response wavelengths emitted by the material sample are captured in response to the optical excitation light wavelength bands. Output values of a plurality of pixels of an image from the imaging sensor are measured, where the image represents excitation response wavelengths captured by the imaging sensor. An output signature indicative of composition of the material sample is generated.

In order to determine a treatment that is best suited to a wound such as an infected wound, a variety of factors can be determined. These factors, which in embodiments can include ten to twenty factors, can work together to promote healing. Typically, no one treatment addresses all of the factors. The system block diagram 600 shows a basic overview of key factors associated with a wound, signaling pathways, and immigrant and resident dermal cells that can coordinate reparative and regenerative responses of wound healing. A wound image can be analyzed and wound exudate can be analyzed to determine one or more biomarkers. The wound exudate can be obtained from a bandage associated with a patient, beneath a film, present in a negative pressure system, and so on. The wound exudate can be analyzed in a laboratory, a bed-side assay, etc. In embodiments, an assay array can be used to detect molecules of interest to determine wound healing. The molecules of interest can include key saccharides and proteins such as glucan, IL1β, IL6, TNF, pH, MMP1, MMP2, MMP8, MMP9, MMP13, TGFβ1, Angiopoietin-1, Angiopoietin-2, Angiogenin, endostatin, CD105, CD31, GM-CSF, TIMP1-4, hyaluronic acid, Collagens I/III/IV, IL10, VEGF, HB-EGF, EGF, PDGF, and so on.

In the system block diagram 600, an individual's insult and resulting innate and adaptive immune responses can stimulate microvascular leakage, signaling neutrophils and monocyte/macrophages to a wound site 610. Glucan synthesis 620 can occur and support inflammatory macrophages 622. In addition, hyaluronic acid synthesis 640 can occur and repair macrophages are borne 642. Transforming growth factor beta (TGF B) can be released from repair macrophages 630 and affect fibroblasts at the wound site. Platelets, fibroblasts, and vascular cells contribute to platelet-derived growth factor (PDGF) 628 and several other growth factor production, e.g. FGF, VEGF, etc. Fibroblasts, vascular cells, and macrophages produce protease matrix metalloproteinases (MMPs) 626, which are affected by the local pH 624. The fibroblasts and vascular cells can also influence hyaluronic acid synthesis 640 and the production of collagen 638. The pH 634 can also affect microbial proliferation, oxygen (O2) 636 levels, which have a bearing on collagen synthesis, and basement membrane assembly (when pH is optimal for healing). The collagen 638 affects blood vessels 646 as well. Repair macrophages 642 can in turn affect both PDGF 628 and vascular endothelial growth factor (VEGF) 644. Thus even the basic overview dermis healing system block diagram 600 shows how complex the process is.

Figure 7:
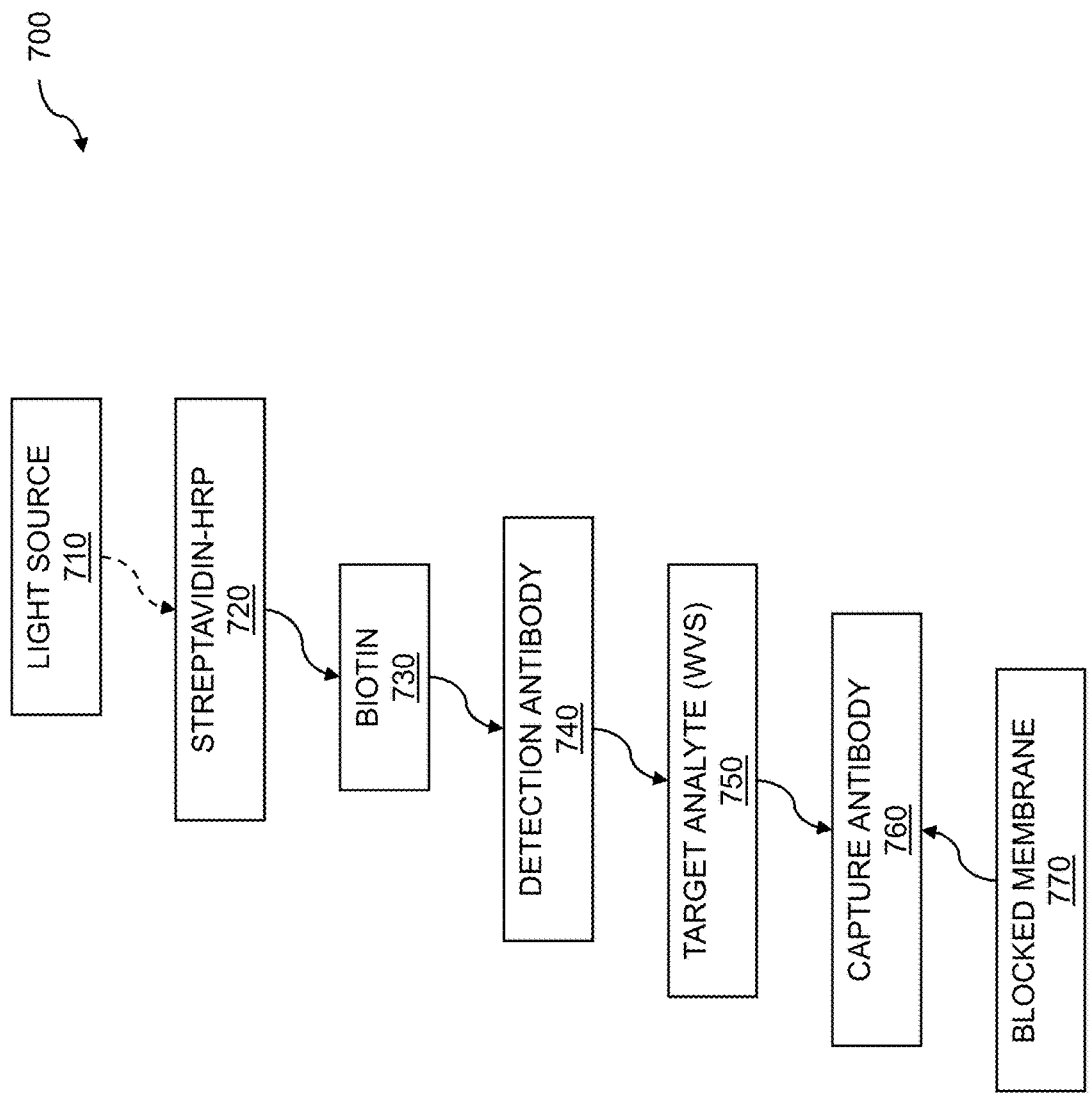
FIG. 7 is a system block diagram for antibody detection.

FIG. 7 is a system block diagram for antibody detection. An array such as the array shown in 700 can be used for antibody detection. Antibody detection can be used to identify molecules such as glucan, IL1β, IL6, TNF, pH, MMP1, MMP2, MMP8, MMP9, MMP13, TGFβ1, Angiopoietin-1, Angiopoietin-2, Angiogenin, endostatin, CD105, CD31, GM-CSF, TIMP1-4, hyaluronic acid, Collagens I/III/IV, IL10, VEGF, HB-EGF, EGF, PDGF, and so on. Antibody detection enables skin diagnostics using optical signatures. A plurality of optical excitation light wavelength bands is scanned on a material sample, wherein the material sample exhibits optical spectral characteristics along the light wavelength spectrum. Excitation response wavelengths emitted by the material sample are captured in response to the plurality of optical excitation light wavelength bands, wherein the capturing is accomplished using an imaging sensor. Output values of a plurality of pixels of an image from the imaging sensor are measured, wherein the image represents excitation response wavelengths captured by the imaging sensor, wherein the measuring detects optical spectral characteristics of the material sample, and wherein the optical spectral characteristics are in response to the plurality of optical excitation light wavelength bands. An output signature indicative of composition of the material sample is generated, wherein the output signature is based on interpreting the output values that were measured.

The system block diagram for antibody detection 700 includes a light source 710. The light source can include a plurality of optical excitation light wavelength bands, where the wavelength bands can include visible light, IR light, LWIR light (heat), and so on. Bioluminescence can be created using horseradish peroxidase (HRP) and hydrogen peroxide. The bioluminescence can be detected by a camera, photographic film, etc. Streptavidin 720 can be used to bind to a biotin 730 with strong affinity. A detection antibody 740 can be in a specific and known location on a material sample such as skin, on a patient's body part, and so on. Thus, light due to bioluminescence or the emission from a fluorophore can be emitted from the specific and known location can indicate that a target analyte 750 has been captured 760. In embodiments, indication that the target antibody has been captured can be based on parameters such as vital signs associated with the wound (WVS). A blocked membrane 770 can be used to support the antibody detection array. The blocked membrane can be used to capture and identify target molecules.

Figure 8:
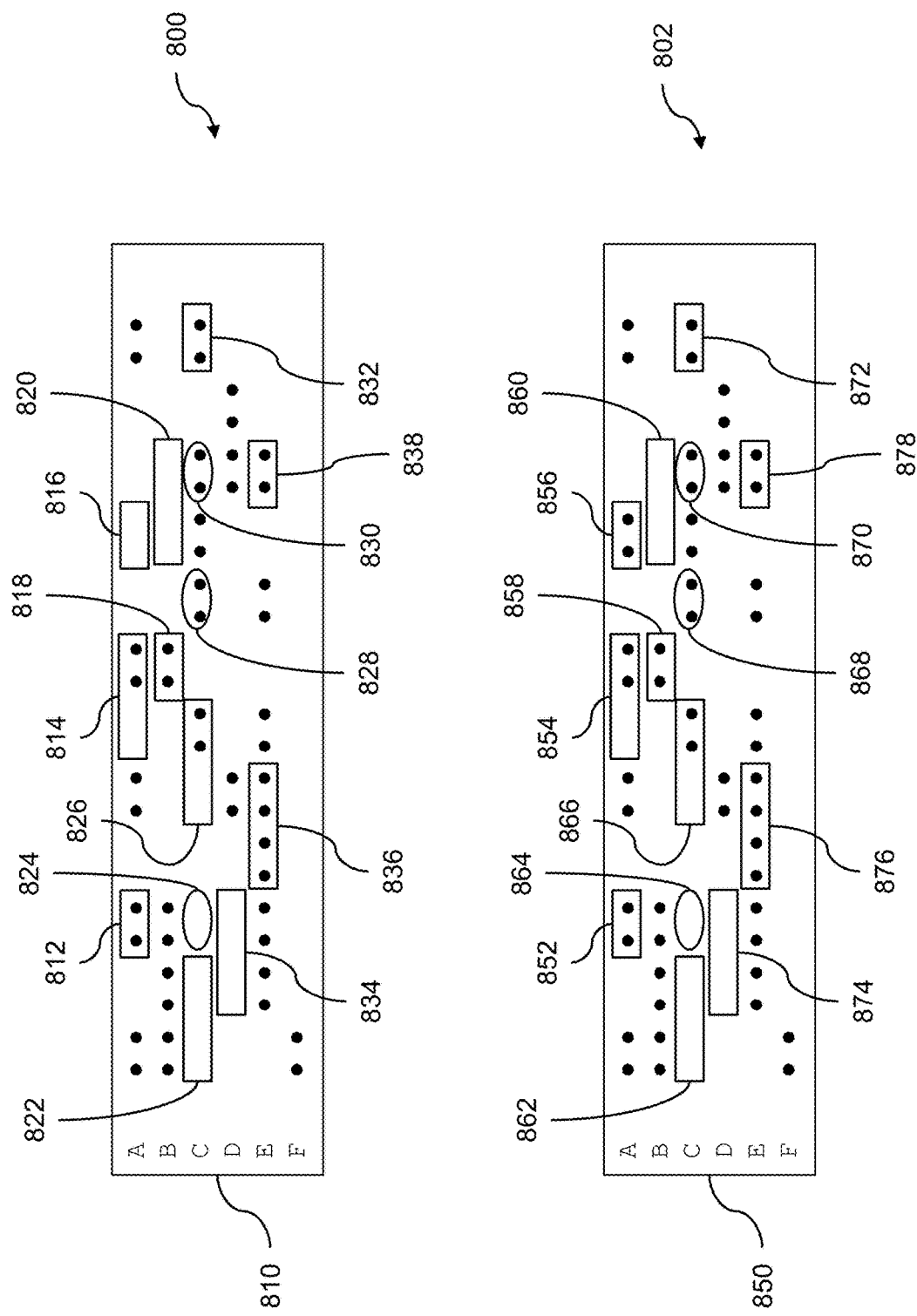
FIG. 8 illustrates an antibody array.

FIG. 8 illustrates an antibody array. An antibody array can show one or more wound parameters or vital signs associated with a wound. The antibody array can be determined for one or more locations associated with a wound such as a wound perimeter, a wound center, etc. The antibody array enables skin diagnostics using optical signatures. Optical excitation light wavelength bands on a material sample are scanned. Excitation response wavelengths emitted by the material sample are captured in response to the plurality of optical excitation light wavelength bands using an imaging sensor. Output values of a plurality of pixels of an image from the imaging sensor are measured. The image represents excitation response wavelengths captured by the imaging sensor. An output signature indicative of composition of the material sample is generated, where the output signature is based on interpreting the measured output values.

Antibody arrays are shown for a wound center 800 and a wound perimeter 802. The antibody arrays can be based on analysis results of wound fluid or exudate, i.e., a liquid biopsy collected from the wound center 810, wound perimeter 850, and so on. Such assays can be performed to determine the state of healing of a wound based on the absence or presence, together with the relative abundance of one or several wound controllers, classifiers or variables controlling healing stages and wound state. Such assays are useful for gauging healing of a wound such as a slow-healing wound, because the rate of healing of the wound can vary across the wound. Fourteen parameters are shown for the example assays of exudate at the wound center and the wound perimeter. More or fewer parameters may be used for the comparison of assay results. The parameters can include Activin A 812 and 852; Angiopoietin 1 and Ang 2 814 and 854; and Amphiregulin 816 and 856. Note the difference between the assay results 816 and 856. This difference can indicate that the perimeter of the wound is healing while the center of the wound is not healing or is only slowly healing. The parameters can further include Endostatin/Collagen XVIII 818 and 858; Fibroblast Growth Factors (FGF) FGF 1 and FGF 2 820 and 860; Glial cell line-derived neurotrophic factors (GDNF) and Granulocyte-macrophage colony-stimulating factors (GM-CSF) 822 and 862. The factors can further include Heparin-binding epidermal growth factor-like (HB-EGF) factors 824 and 864; Insulin-like growth factor-binding proteins (IGFBP) IGFBP 1 and IGFBP 2 826 and 866; Interleukin 1 Beta 828 and 868; and Transforming growth factor betas (TGFb-1) 830 and 870. The factors can also include Monocyte chemoattractant protein 1 (MCP-1) 832 and 872; Matrix metalloproteinases (MIPs) MMP8 and MMP9 834 and 874; Tissue inhibitors of metallopeptidase (TIMP) TIMP1 and TIMP4 836 and 876: and Vascular endothelial growth factors (VEGF) 838 and 878. As noted above, one or more factors can be present or absent at a wound location such as a wound center, a wound perimeter, and so on. Note further that the magnitude of a given parameter can vary across the wound, temporally and spatially, and that these amplitude modulations influence the stage of healing and the wound state, while classifying each. Such differences in magnitude can also be indicative of causes for a wound to be slow healing or nonhealing.

Figure 9:
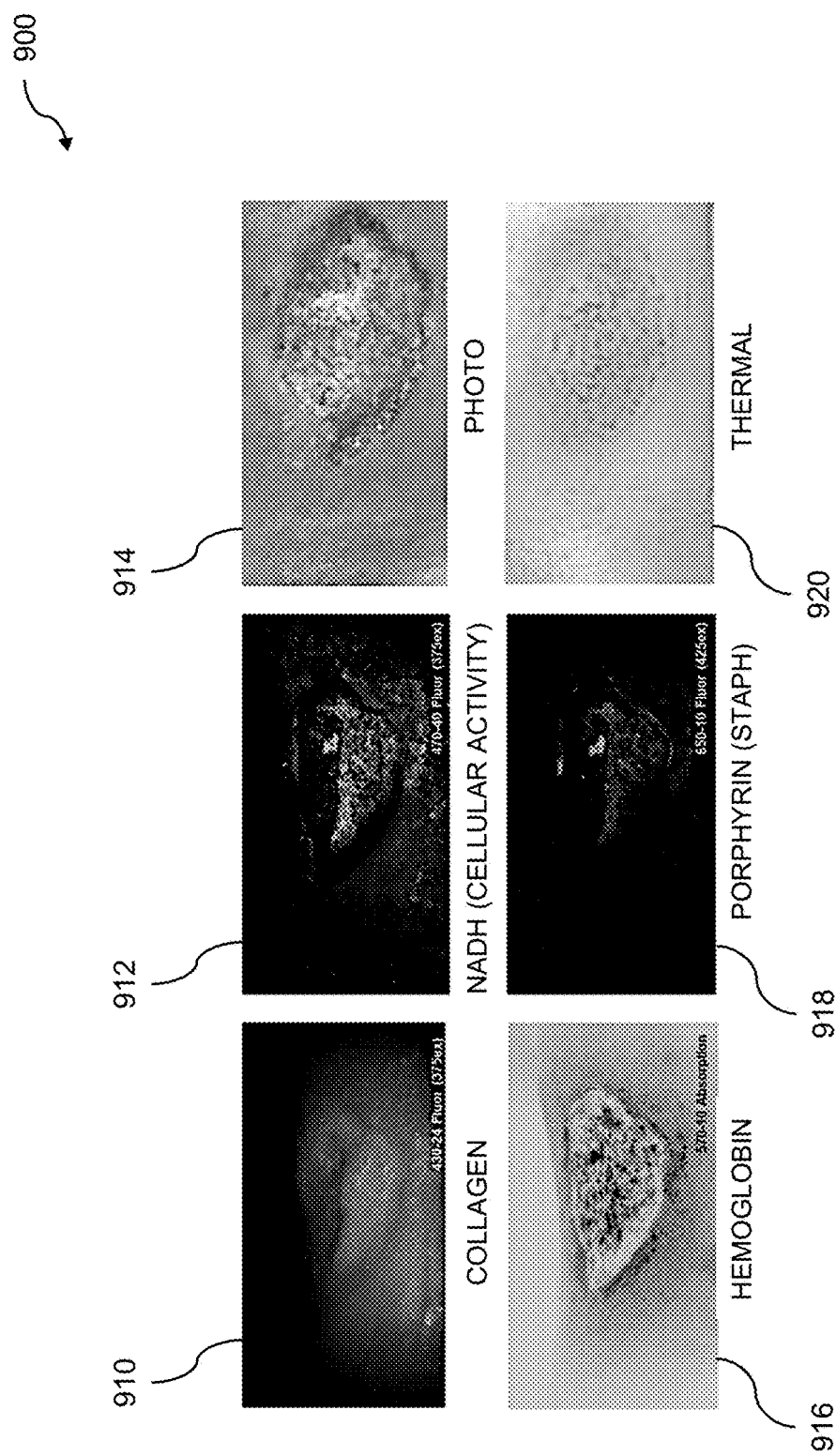
FIG. 9 shows images for infection detection and analysis of wound state.

FIG. 9 shows images for infection detection and analysis of wound state. One or more images can be obtained and analyzed for infection detection. The images can be based on fluorescence, absorption, and so on, of a material sample such as tissue scanned with one or more optical excitation light wavelength bands. The images enable skin diagnostics using optical signatures. A plurality of optical excitation light wavelength bands is scanned on a material sample, where the material sample exhibits optical spectral characteristics along the light wavelength spectrum. Excitation response wavelengths emitted by the material sample are captured in response to the plurality of optical excitation light wavelength bands, where the capturing is accomplished using an imaging sensor. Output values of a plurality of pixels of an image from the imaging sensor are measured, where the image represents excitation response wavelengths captured by the imaging sensor, where the measuring detects optical spectral characteristics of the material sample, and where the optical spectral characteristics are in response to the plurality of optical excitation light wavelength bands. An output signature indicative of composition of the material sample is generated, where the output signature is based on interpreting the output values that were measured.

Images which have been collected and analyzed can be used for infection detection 900. The images can be based on fluorescence response wavelengths, absorption response wavelengths, and so on, where the response wavelengths can be emitted by the material sample in response to exposer by the various optical excitation light wavelength bands. Note that the emitted response wavelengths can be different from the excitation light wavelengths scanned on the material sample. In embodiments, a first band of the plurality of optical excitation light wavelength bands can include wavelengths substantially in the range of 325 nm to 375 nm, a second band of the plurality of optical excitation light wavelength bands can include wavelengths substantially in the range of 350 nm to 400 nm, and a third band of the plurality of optical excitation light wavelength bands can include wavelengths substantially in the range of 375 nm to 425 nm. Other bands of optical excitation light wavelength bands can further be used. In embodiments, a fourth band of the plurality of optical excitation light wavelength bands can include wavelengths substantially in the range of 400 nm to 450 nm. An output signature can be interpreted from emission detected from the scanned material sample. In embodiments, the interpreting can be based on measured wavelengths substantially in the range of 400 nm to 460 nm. Other fluorescence excitation light wavelength bands can be used to expose the material sample. Further embodiments include exposing the material sample to a fluorescence excitation light wavelength band comprising wavelengths substantially in the 315 nm to 375 nm range to augment the interpreting. Image 910 can be based on 375 nm excitation with 430 nm emission, where the 430 nm emission or output signature can be indicative of the presence of collagen.

Image 912 can be based on 375 nm excitation with 470 nm output signature can be indicative of the presence of nicotinamide adenine dinucleotide plus hydrogen (NADH) and flavins. An image can include photograph 914. The photograph can be based on visible light, where visible light can include wavelengths substantially within the approximate range of 380 nm and 750 nm. The images can be based on absorption. Image 916 can be based on 570 nm absorption, where the 570 nm absorption can be indicative of hemoglobin. The images can further be based on narrow bands. In embodiments, the plurality of optical excitation light wavelength bands can include narrow bands substantially at 350 nm, 375 nm, 400 nm, 425 nm, 450 nm, 500 nm, 525 nm, 550 nm, 575 nm, 600 nm, and 625 nm. Other embodiments can include exposing the material sample to a narrow fluorescence excitation light wavelength band comprising wavelengths substantially at 400 nm to augment the interpreting. The interpreting can be based on additional measured wavelengths. In embodiments, the interpreting can be based on measured wavelengths substantially in the range of 600 nm to 660 nm and 675 nm to 725 nm. Image 918 can be based on 425 nm excitation and 650 nm emission which can be analyzed to generate an output signature. In embodiments, the output signature can be indicative of the presence of porphyrins. Longer wavelengths can also be used to analyze the material sample. Image 920 can be based on the magnitude of photons between 7 and 15 microns that are detected, which can create a monochromatic image where intensity is converted into temperature, and where the intensity represents a thermal profile of the wound. In embodiments, the interpreting is based on excitation wavelengths from 380 nm to 420 nm and measured wavelengths substantially in the range of 500 nm to 550 nm and 550 nm to 600 nm. In embodiments, the output signature is indicative of the presence of pyoverdine, based on a ratio of output values from the range of 550 nm to 600 nm to output values from the range of 500 nm to 550 nm.

FIG. 10 is a table showing biochromes and fluorescent channels. A fluorophore is a chemical compound that when excited by light, re-emits light. Biochromes include substances such as chemical compounds which present a color based on selective absorption of other colors. The colors are based on wavelengths of light. Biochromes and fluorescent channels support skin diagnostics using optical signatures. A plurality of optical excitation light wavelength bands is scanned on a material sample. Excitation response wavelengths emitted by the material sample are captured in response to the plurality of optical excitation light wavelength bands. Output values of a plurality of pixels of an image from the imaging sensor are measured. An output signature indicative of composition of the material sample is generated, where the output signature is based on interpreting the output values that were measured.

A table based on biochromes and fluorescent channels is shown 1000. The table includes skin fluorophores and biochromes 1010. Each of the skin fluorophores and biochromes can correspond to a factor associated with healing. Each of the factors can further be associated with one or more biomolecules or cell localizations 1012. The various skin fluorophores and biochromes can be excited by an optical excitation light wavelength band 1014. The excited fluorophores and biochromes generate an emission response 1016 by the scanned material sample. In embodiments, the material sample can include cells, tissues, and organs. The material sample can include skin, lungs, and so on. The emission response can be indicative of infection such as infection of a wound, respiratory infection such as a COVID-19 infection or influenza infection, residual cancer detection, and so on.

FIG. 11 is a table showing cells associated with hemostasis and wound healing. A wound to skin, an organ, and so on, can cause prodigious bleeding. The first step to healing the wound is to stanch the bleeding. Hemostasis is a process that stops bleeding and prevents further bleeding based on blood platelet function and coagulation of blood, where coagulation includes transforming blood from a liquid to a gel. The coagulating or clotting of the blood is dependent on functional blood platelets, which become activated, releasing many factors that control downstream effectors, which influence vascular leakage, immune responses and the reparative/regenerative responses needed for healing. Hemostasis and wound healing can be analyzed using skin diagnostics using optical signatures. A plurality of optical excitation light wavelength bands is scanned on a material sample, where the material sample exhibits optical spectral characteristics along the light wavelength spectrum. Excitation response wavelengths emitted by the material sample in response to the plurality of optical excitation light wavelength bands are captured, where the capturing is accomplished using an imaging sensor. Output values of a plurality of pixels of an image from the imaging sensor are measured, where the image represents excitation response wavelengths captured by the imaging sensor, where the measuring detects optical spectral characteristics of the material sample, and where the optical spectral characteristics are in response to the plurality of optical excitation light wavelength bands. An output signature indicative of composition of the material sample is generated, wherein the output signature is based on interpreting the output values that were measured.

Table 1100 shows various cells that can be associated with hemostasis and the various stages and state of wound healing. The table shows resident cells 1110, where the resident cells can be present in blood, tissue, and so on. The resident cells can produce key products 1112, where the key products can signal and modulate healing. The healing can include healing of a wound such as a tissue wound or an organ wound; recovery from an infection such as an infection of the skin or organ, or a respiratory infection such as COVID-19 or influenza; detection to facilitate removal of residual cancer; and so on. The key products can be associated with target cell or cell function 1114. The target cell or cells can be associated with wound healing, infection recovery, and the like.

FIG. 12 is a table showing immune surveillance cells. The immune system associated with an individual fights "foreign invaders" to their body. The foreign invaders can include bacteria, fungi, viruses, tumors, and so on. The immune system identifies and attempts to eliminate the invading pathogen(s), whether fungi, bacteria, viruses, etc. based on immune surveillance. For example, a tumor can include cells that are based on transformed normal cells. The transformed cells associated with tumor-expressed antigens, where the expressed antigens are not found in normal cells. As a result, the body attacks with immune cells the self-antigens as 'foreign' antigens. Immune surveillance can be analyzed using skin diagnostics using optical signatures. A plurality of optical excitation light wavelength bands is scanned on a material sample. Excitation response wavelengths emitted by the material sample are captured in response to the plurality of optical excitation light wavelength bands. Output values of a plurality of pixels of an image from the imaging sensor are measured, and an output signature indicative of composition of the material sample is generated.

A table showing immune surveillance cells, key products, and one or more target cells is shown 1200. Some symptoms or conditions presented by a patient can appear similar to those caused by infection, but can actually be caused by autoimmune disorders, as above. One identifier that differentiates between an infection and an autoimmune disorder can include an absence of infecting microbes or non-specific inflammation, e.g., vasculitis, which is associated with the autoimmune disorder (e.g. gangrenosum pyoderma). Careful diagnosis can be required to differentiate between an autoimmune disorder, which may be treated with an immune suppression technique, and an infection which may be treated by boosting immunity, prescribing antibiotics, and so on. Various immune surveillance cells are shown 1210. The cells can be associated with one or more key products 1212. The key products can be used to elicit effector or target cell function 1214, where the target cells can be attacked, used to fight infection, used to rebuild tissue, and so on.

Figure 13:
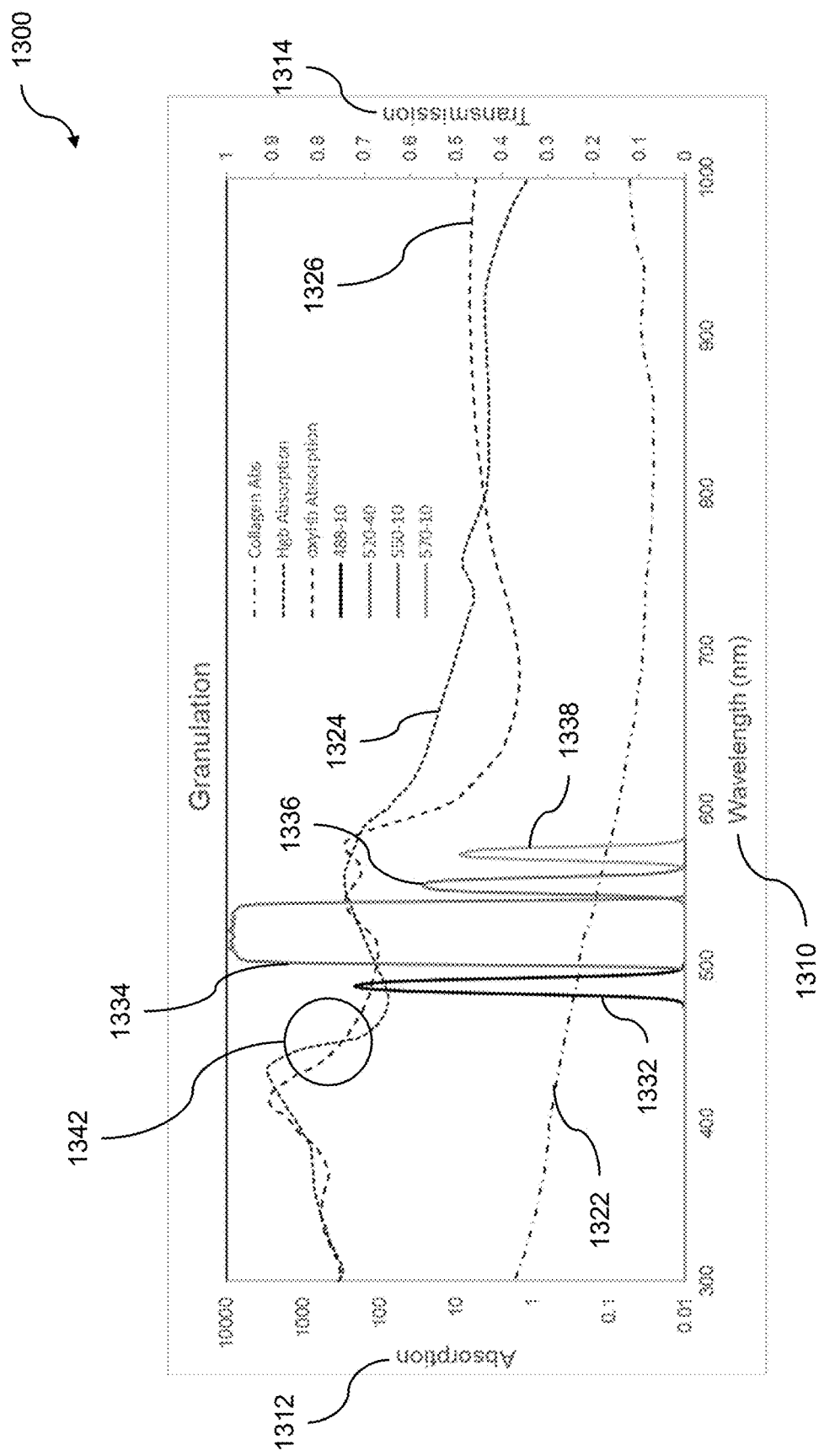
FIG. 13 shows granulation identification.

FIG. 13 shows granulation identification. Using disclosed techniques, the graph 1300 shows an output signature for identifying granulation in tissue. Output signature usage is enabled by skin diagnostics using optical signatures. A plurality of optical excitation light wavelength bands is scanned on a material sample. The material sample can include cells, tissues, and organs. Excitation response wavelengths emitted by the material sample are captured in response to the plurality of optical excitation light wavelength bands. Output values of a plurality of pixels of an image from the imaging sensor are measured, and an output signature indicative of composition of the material sample is generated.

In the graph 1300, an x-axis indicating wavelength 1310 is provided. Increasing wavelength from left to right indicates decreasing frequency of light waves and a traversal from the ultraviolet spectrum, approximately sub-400 nm, through the blue, green, and red wavelength regions, roughly 450 nm, 550 nm, and 650 nm, respectively, to the infrared wavelength band, which is roughly greater than 750 nm. It should be noted that an exact wavelength definition of a particular color is somewhat arbitrary and is dependent on the sensor type. For example, the cones of a human eye roughly sense RGB signals using three cone types, but they are generally distributed differently from a typical CMOS RGB sensor's output. However, maintaining a consistent definition for a given system is generally required in order to provide consistent sample indications. The graph 1300 also includes a left y-axis of absorption amount 1312 and a right y-axis of transmission amount 1314.

The graph 1300 includes absorption characteristics, such as absorption characteristic 1322, typical for the presence of collagen, absorption characteristic 1324, typical for the presence of hemoglobin (Hgb), and absorption characteristic 1326, typical for the presence of oxygenated hemoglobin (oxyHb). The typical absorption characteristics 1322, 1324, and 1326 can be used as reference signals as is, or they can be compensated to enable generation of an indication of material composition. A granulation output signature is isolated by quantifying the dip in the Hgb spectrum at 450 nm, illustrated in highlight circle 1342. Tissue that is mostly collagen will not have a dip, whereas granulation tissue will have a dip that resides roughly halfway between the typical Hgb characteristic 1324 and/or 1326 and the typical collagen characteristic 1322. The intensity of the dip can be quantified by taking the ratio or difference of the absorption intensity at 1336 and/or 1338 and comparing it to the absorption intensity at 1334 and/or 1332.

The graph 1300 shows signals indicative of filter characteristics, including signals 1332, 1334, 1336, and 1338. Signal 1332 represents a light wavelength centered at about 488 nm with a bandwidth of about 10 nm and a relative transmission amplitude of about 0.7 out of 1. Signal 1334 represents a light wavelength centered at about 520 nm with a bandwidth of about 40 nm and a relative transmission amplitude of almost 1.0 out of 1. Signal 1336 represents a light wavelength centered at about 550 nm with a bandwidth of about 10 nm and a relative transmission amplitude of about 0.6 out of 1. Signal 1338 represents a light wavelength centered at about 570 nm with a bandwidth of about 10 nm and a relative transmission amplitude of about 0.5 out of 1. It is to be understood that the characteristics and signals illustrated herein have substantially the values shown in graph 1300, but that normal, typical variations and equipment calibration may provide a delta to the characteristics and signals, such as a five percent delta.

Figure 14:
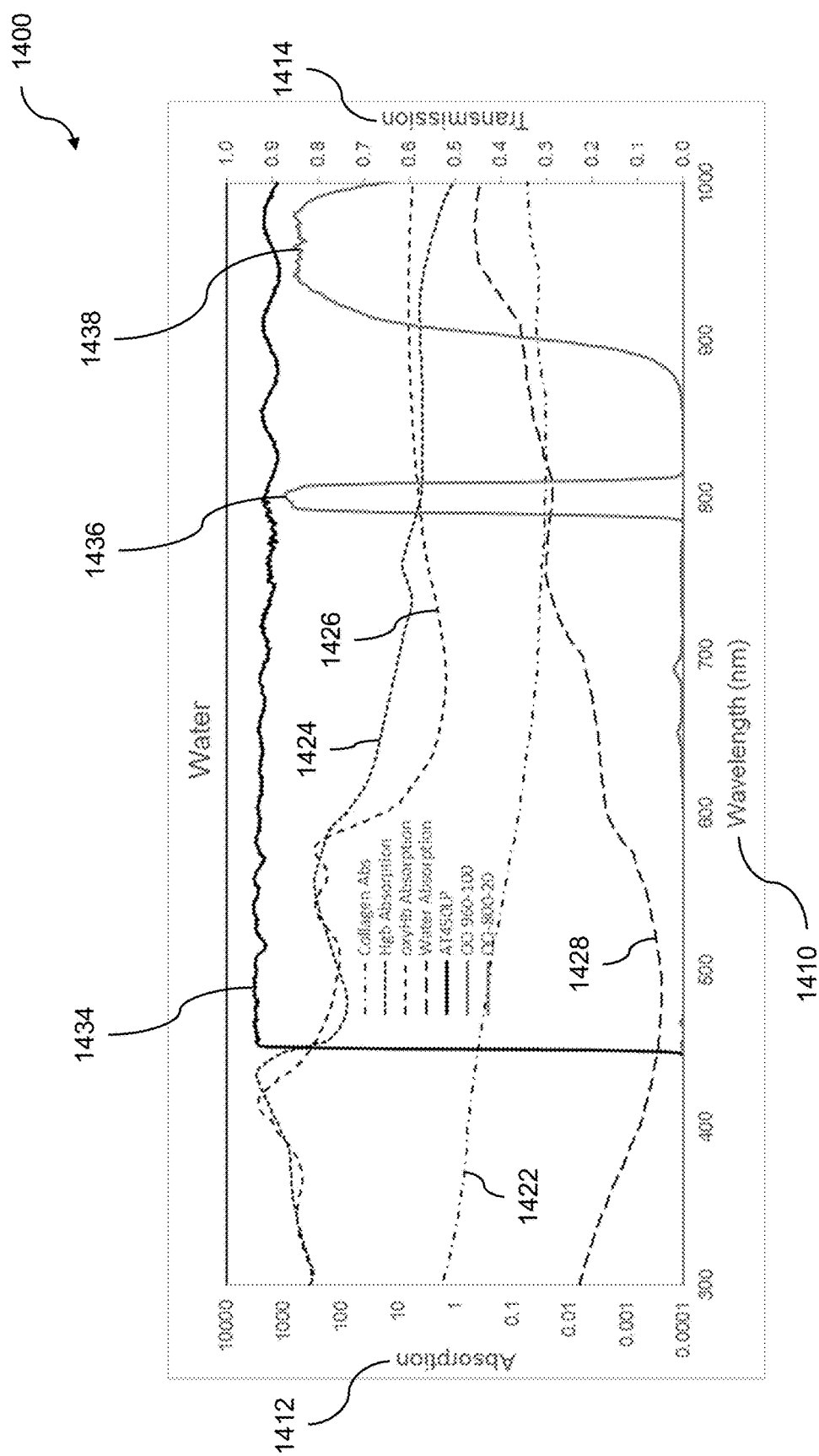
FIG. 14 illustrates water identification.

FIG. 14 shows water identification. Using disclosed techniques, the graph 1400 shows an output signature for identifying the presence of water in tissue. Output signature usage is enabled by skin diagnostics using optical signatures. A plurality of optical excitation light wavelength bands is scanned on a material sample. The material sample can include cells, tissues, and organs. Excitation response wavelengths emitted by the material sample are captured in response to the plurality of optical excitation light wavelength bands. Output values of a plurality of pixels of an image from the imaging sensor are measured, and an output signature indicative of composition of the material sample is generated.

In the graph 1400, an x-axis indicating wavelength 1410 is provided. Increasing wavelength from left to right indicates decreasing frequency of light waves and a traversal from the ultraviolet spectrum, roughly sub-400 nm, through the blue, green, and red wavelength regions, roughly 450 nm, 550 nm, and 650 nm, respectively, to the infrared wavelength band, which is roughly greater than 750 nm. It should be noted that an exact wavelength definition of a particular color is somewhat arbitrary and dependent on the sensor type. For example, the cones of a human eye roughly sense RGB signals using three cone types, but they are generally distributed differently from a typical CMOS RGB sensor's output. However, maintaining a consistent definition for a given system is generally required in order to provide consistent sample indications. The graph 1400 also includes a left y-axis of absorption amount 1412 and a right y-axis of transmission amount 1414.

The graph 1400 includes absorption characteristics, such as absorption characteristic 1422, indicative of the presence of collagen, absorption characteristic 1424, indicative of the presence of hemoglobin (Hgb), absorption characteristic 1426, indicative of the presence of oxygenated hemoglobin (oxyHb), and absorption characteristic 1428, indicative of the presence of water. The typical absorption characteristics 1422, 1424, 1426, and 1428 can be used as reference signals as is, or they can be compensated to enable generation of an indication of material composition. A water output signature is isolated by irradiating a material sample (wound or other) with broad-band white light and comparing the absorption at 960 nm (or similar) and 800 nm (or similar). In the graph 1400, broad-band white light is passed by a long-pass filter, shown as signal 1434, which cuts off wavelengths of light below 450 nm (in the ultraviolet range), and allows visible light above 450 nm with a relative transmission amplitude of about 0.9 out of 1. Light emanating from the sample can be measured at two or more points at successively longer wavelengths, as shown by signals 1436 and 1438. Signal 1436 represents an optical filter centered at about 800 nm with a bandwidth of about 20 nm and a relative amplitude of about 0.85 out of 1. Signal 1438 represents a light wavelength centered at about 960 nm with a bandwidth of about 100 nm and a relative amplitude of about 0.85 out of 1. The output signature of water will be substantially higher at the longer wavelength sample point. As shown in graph 1400, this is not true for the absorption characteristics of collagen 1422 and hemoglobin 1424 and 1426 as sampled at 800 nm and 960 nm. It is to be understood that the characteristics and signals have substantially the values illustrated in graph 1400, but that normal, typical variations and equipment calibration may provide a delta to the characteristics and signals, such as a five percent delta.

Figure 15:
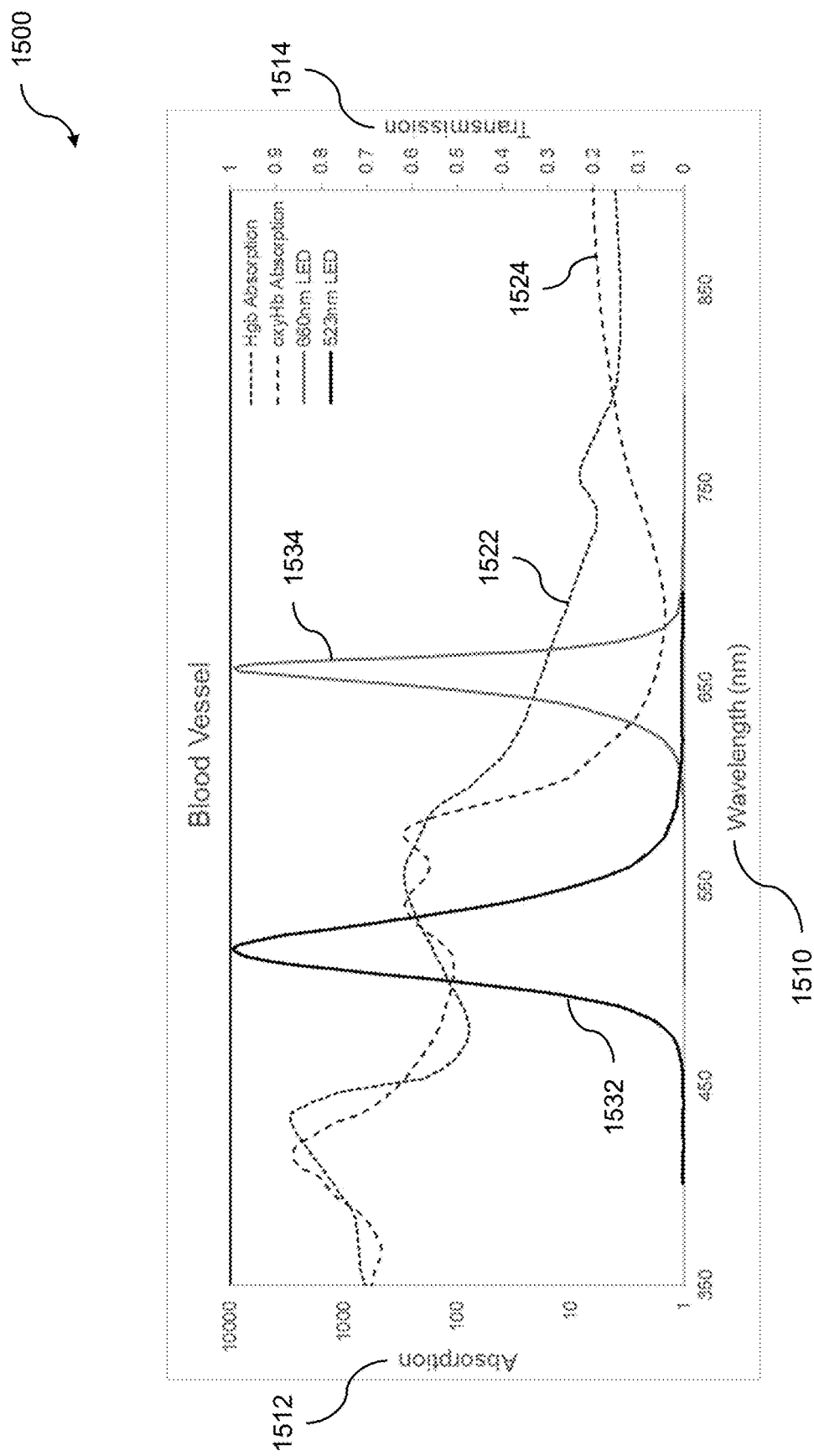
FIG. 15 shows blood vessel identification.

FIG. 15 shows blood vessel identification. Using disclosed techniques, the graph 1500 shows an output signature for identifying the presence of blood vessels in tissue. Output signature usage is enabled by skin diagnostics using optical signatures. A plurality of optical excitation light wavelength bands is scanned on a material sample. The material sample can include cells, tissues, and organs. Excitation response wavelengths emitted by the material sample are captured in response to the plurality of optical excitation light wavelength bands. Output values of a plurality of pixels of an image from the imaging sensor are measured, and an output signature indicative of composition of the material sample is generated.

In the graph 1500, an x-axis indicating wavelength 1510 is provided. Increasing wavelength from left to right indicates decreasing frequency of light waves and a traversal from the ultraviolet spectrum, roughly sub-400 nm, through the blue, green, and red wavelength regions, roughly 450 nm, 550 nm, and 650 nm, respectively, to the infrared wavelength band, which is roughly greater than 750 nm. It should be noted that an exact wavelength definition of a particular color is somewhat arbitrary and dependent on the sensor type. For example, the cones of a human eye roughly sense RGB signals using three cone types, but they are generally distributed differently from a typical CMOS RGB sensor's output. However, maintaining a consistent definition for a given system is generally required in order to provide consistent sample indications. The graph 1500 also includes a left y-axis of absorption amount 1512 and a right y-axis of transmission amount 1514.

The graph 1500 includes absorption characteristics, such as absorption characteristic 1522, indicative of the presence of hemoglobin (Hgb), and absorption characteristic 1524, indicative of the presence of oxygenated hemoglobin (oxyHb). The typical absorption characteristics 1522 and 1524 can be used as reference signals as is, or they can be compensated to enable generation of an indication of material composition. A blood vessel signal is isolated based on the absorption of Hgb at 523 nm and 660 nm. Light from two different light emitting diodes (LEDs) is used to illumine a material sample. In the graph 1500, signal 1532 represents the typical output spectrum of a 523 nm LED, and signal 1534 represents the typical output spectrum of a 660 nm LED. As can be seen in graph 1500, the absorption characteristics of Hgb 1522 and oxyHb 1524 are very similar at about 523 nm. However, an order of magnitude difference is observed when comparing absorption characteristics 1522 and 1524 at 660 nm. The low absorption in the red band is indicative of oxygenated hemoglobin, which is typically found in active blood vessels, but not found in pooled blood due to bruising or other wound-related phenomena. It is to be understood that the characteristics and signals have substantially the values illustrated in graph 1500, but that normal, typical variations and equipment calibration may provide a delta to the characteristics and signals, such as a five percent delta.

Figure 16:
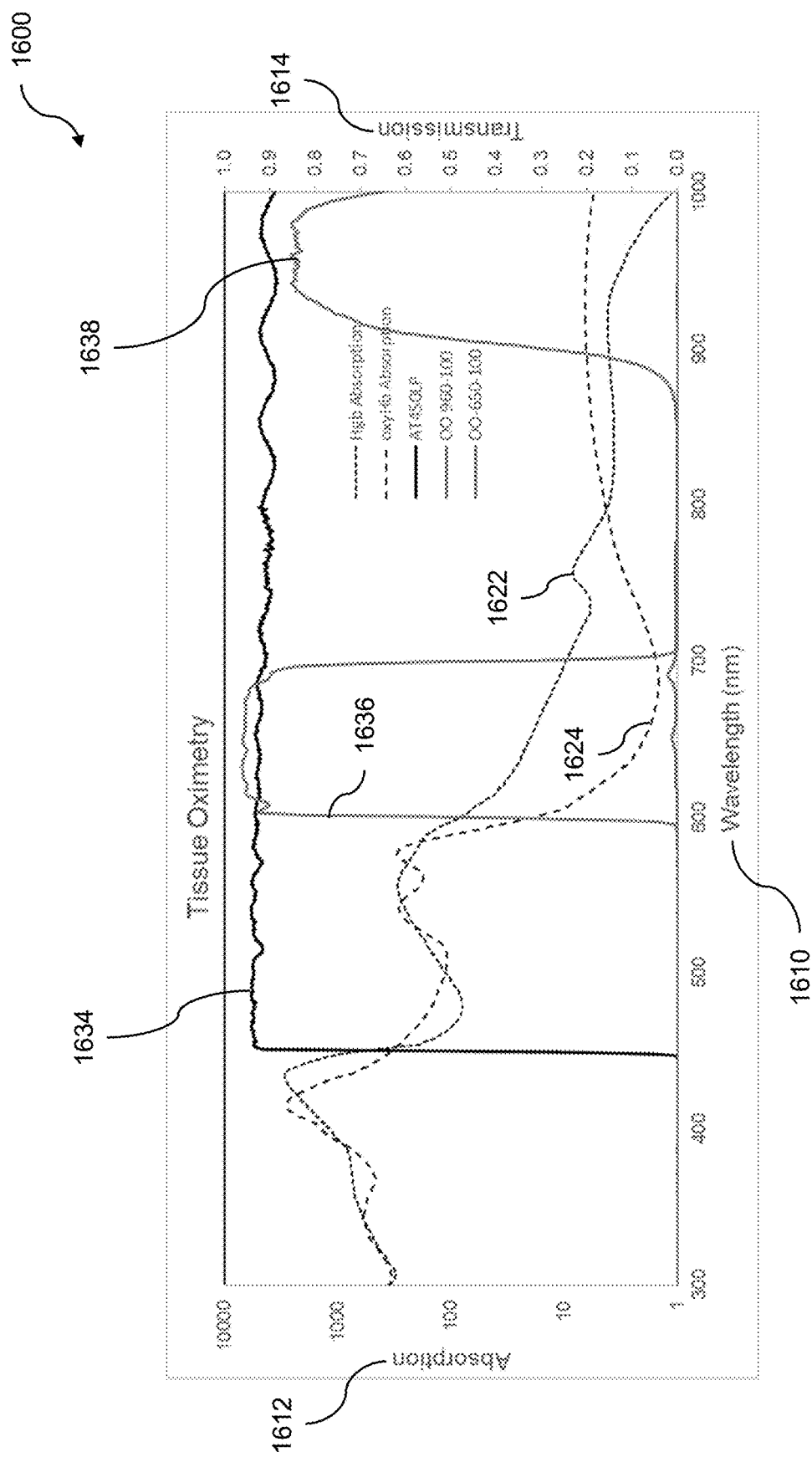
FIG. 16 illustrates tissue oximetry.

FIG. 16 shows tissue oximetry. Using disclosed techniques, the graph 1600 shows an output signature for identifying the presence of oxygen in tissue. Output signature usage is enabled by skin diagnostics using optical signatures. A plurality of optical excitation light wavelength bands is scanned on a material sample. The material sample can include cells, tissues, and organs. Excitation response wavelengths emitted by the material sample are captured in response to the plurality of optical excitation light wavelength bands. Output values of a plurality of pixels of an image from the imaging sensor are measured, and an output signature indicative of composition of the material sample is generated.

In the graph 1600, an x-axis indicating wavelength 1610 is provided. Increasing wavelength from left to right indicates decreasing frequency of light waves and a traversal from the ultraviolet spectrum, roughly sub-400 nm, through the blue, green, and red wavelength regions, roughly 450 nm, 550 nm, and 650 nm, respectively, to the infrared wavelength band, which is roughly greater than 750 nm. It should be noted that an exact wavelength definition of a particular color is somewhat arbitrary and dependent on the sensor type. For example, the cones of a human eye roughly sense RGB signals using three cone types, but they are generally distributed differently from a typical CMOS RGB sensor's output. However, maintaining a consistent definition for a given system is generally required in order to provide consistent sample indications. The graph 1600 also includes a left y-axis of absorption amount 1612 and a right y-axis of transmission amount 1614.

The graph 1600 includes absorption characteristics, such as absorption characteristic 1622, indicative of the presence of hemoglobin (Hgb), and absorption characteristic 1624, indicative of the presence of oxygenated hemoglobin (oxyHb). The typical absorption characteristics 1622 and 1624 can be used as reference signals as is, or they can be compensated to enable generation of an indication of material composition. An oxygenated tissue output signature is isolated by comparing absorption at 960 nm, where oxyHb absorption dominates, to 650 nm, where Hgb absorption dominates. In the graph 1600, broad-band white light is passed by a long-pass filter, shown as signal 1634, which cuts off wavelengths of light below 450 nm (in the ultraviolet range), and allows visible light above 450 nm with a relative transmission amplitude of about 0.9 out of 1. Light emanating from the sample can be measured at two or more points at successively longer wavelengths, as shown by signals 1636 and 1638. Signal 1636 represents an optical filter centered at about 650 nm with a bandwidth of about 100 nm and a relative amplitude of about 0.95 out of 1. Signal 1638 represents a light wavelength centered at about 960 nm with a bandwidth of about 100 nm and a relative amplitude of about 0.85 out of 1. The output signature of oxygenated tissue will show higher absorption at the longer wavelength sample point. It is to be understood that the characteristics and signals have substantially the values illustrated in graph 1600, but that normal, typical variations and equipment calibration may provide a delta to the characteristics and signals, such as a five percent delta.

Figure 17:
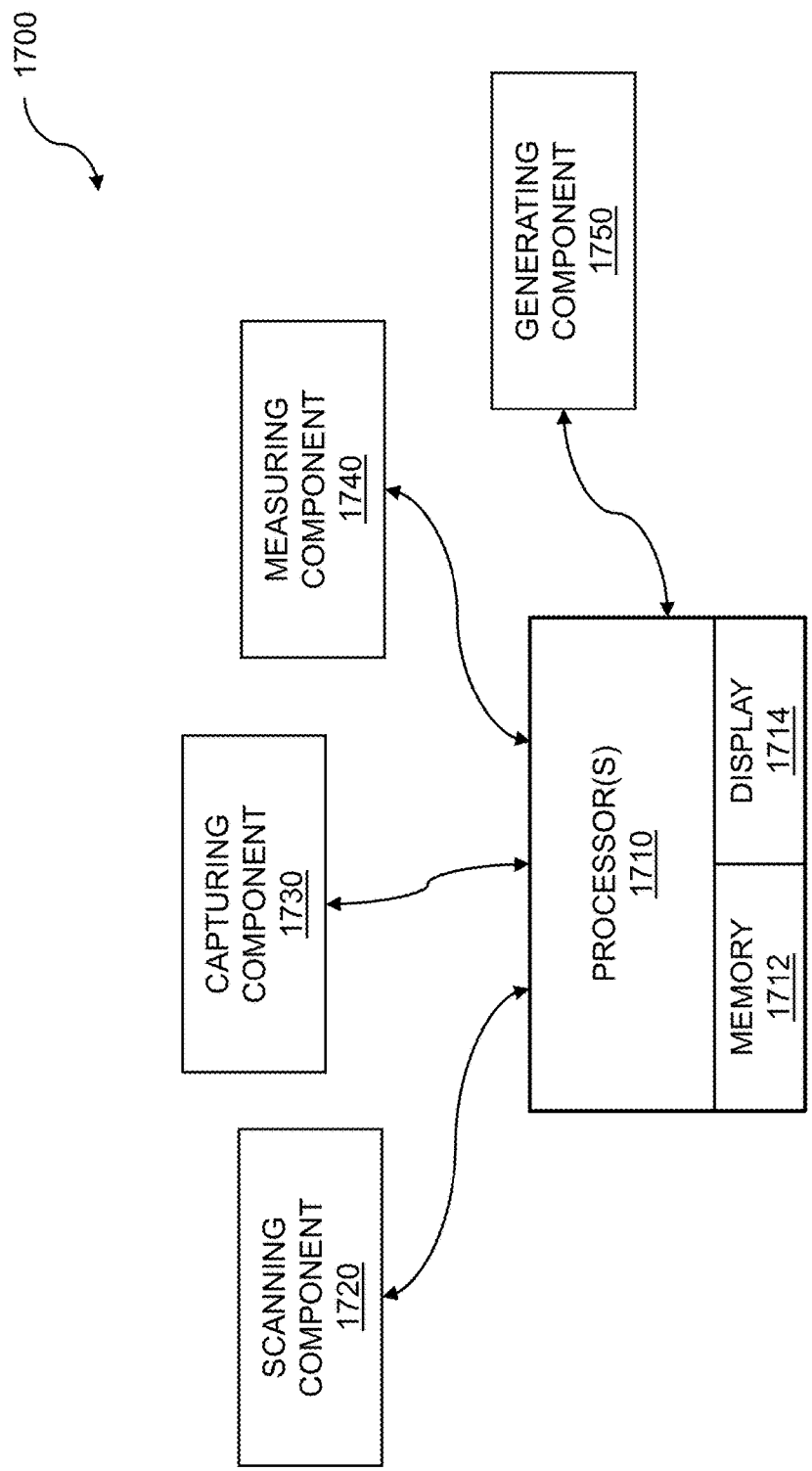
FIG. 17 is a system diagram for skin diagnostics using optical signatures.

FIG. 17 is a system diagram for skin diagnostics using optical signatures. The system 1700 can include one or more processors 1710, which are attached to a memory 1712 which stores instructions. The system 1700 can further include a display 1714 coupled to the one or more processors 1710 for displaying data, indications of sample analysis, directions, input requests, control options, excitation wavelengths, filter options, compensation options, data forwarding options, and so on. Embodiments of the system 1700 comprise a computer system for skin diagnostics comprising: one or more processors 1710 that are coupled to the memory 1712 which stores instructions, wherein the one or more processors, when executing the instructions which are stored, are configured to: scan a plurality of optical excitation light wavelength bands on a material sample, wherein the material sample exhibits optical spectral characteristics along the light wavelength spectrum; capture excitation response wavelengths emitted by the material sample in response to the plurality of optical excitation light wavelength bands, wherein the capturing is accomplished using an imaging sensor; measure output values of a plurality of pixels of an image from the imaging sensor, wherein the image represents excitation response wavelengths captured by the imaging sensor, wherein the measuring detects optical spectral characteristics of the material sample, and wherein the optical spectral characteristics are in response to the plurality of optical excitation light wavelength bands; and generate an output signature indicative of composition of the material sample, wherein the output signature is based on interpreting the output values that were measured.

The system 1700 can include a scanning component 1720. The scanning component 1720 can be used to scan a plurality of optical excitation light wavelength bands on a material sample, where the material sample exhibits optical spectral characteristics along the light wavelength spectrum. Various materials can be scanned. In embodiments, the material sample can include cells, tissues, and organs. The material sample can be collected from a variety of cells, tissues, and organs associated with a patient. In a usage example, the material sample can include healthy tissue, damaged tissue, and so on. In embodiments the material sample can be from a wound. The optical excitation light wavelength bands can be provided by various different sources including an incandescent light source, an LED light source, a laser light source, and so on. The light source or sources can emit a narrow spectrum of light at primarily one wavelength, at primarily two or more wavelengths, across a broad spectrum of multiple wavelengths, in the visible spectrum, in the infrared spectrum, in the ultraviolet spectrum, and so on. The excitation wavelengths can be targeted towards material sample fluorescence or material sample absorption. A fluorescence excitation light wavelength signal can have a wavelength less than a wavelength of the RGB light wavelength spectrum. The wavelength less than a wavelength of the RGB light wavelength spectrum can be substantially between 200 nm and 450 nm. The wavelength bands can include a first band of the plurality of optical excitation light wavelength bands comprising wavelengths substantially in the range of 325 nm to 375 nm, a second band of the plurality of optical excitation light wavelength bands comprising wavelengths substantially in the range of 350 nm to 400 nm, and a third band of the plurality of optical excitation light wavelength bands comprising wavelengths substantially in the range of 375 nm to 425 nm. In embodiments, a fourth band of the plurality of optical excitation light wavelength bands comprises wavelengths substantially in the range of 400 nm to 450 nm.

The system 1700 can include a capturing component 1730. The capturing component 1730 can capture excitation response wavelengths emitted by the material sample in response to the plurality of optical excitation light wavelength bands, where the capturing is accomplished using an imaging sensor. The imaging sensor can include an RGB sensor, an infrared (IR) sensor, and long wavelength IR (LWIR) sensor, an ultraviolet sensor, and so on. In embodiments, a broad band sensor can be used with one or more filters. The system 1700 can include a measuring component 1740. The measuring component 1740 can provide a digital or analog signal output related to output values of a plurality of pixels of an image from the imaging sensor. The measuring can detect optical spectral characteristics of the material sample. The optical spectral characteristics can include fluorescence, absorption, and so on. The optical spectral characteristics can be in response to the plurality of optical excitation light wavelength bands that are scanned on the material sample. In embodiments, the plurality of optical excitation light wavelength bands can include narrow bands substantially at 350 nm, 375 nm, 400 nm, 425 nm, 450 nm, 500 nm, 525 nm, 550 nm, 575 nm, 600 nm, 625 nm, and so on. The output of the measuring can be processed using various signal processing techniques. For example, the measuring component output can be compensated to account for naturally occurring manufacturing differences associated with a sensor by completing a calibration step before the material sample is analyzed.

The system 1700 can include a generating component 1750. The generating component 1750 can generate an output signature indicative of the composition of the material sample. The output signature can be based on interpreting the output values that were measured. The output signature can be indicative of the presence or absence of cells, proteins, and so on. In embodiments, the output signature can be indicative of the presence of nicotinamide adenine dinucleotide plus hydrogen (NADH) and flavins. The interpreting used to generate the output signature can be based on measured wavelengths, where the measured wavelengths can be associated with fluorescence, absorption, and so on. In other embodiments, the output signature can be indicative of the presence of collagen, the presence of porphyrins, and the like. When the output signature is generated for a material sample associated with a wound, the output signature can include microbe indications, inflammation markers, granulation markers, epithelialization markers, and remodeling markers. The output signature can be used for a variety of purposes including wound care management, providing a wound healing trajectory, detecting infection, etc. A detected infection can include a respiratory infection. Further embodiments include regenerating the output signature over time. The output signature can be regenerated based on new parameter values which can be obtained for scanning an additional material sample. In embodiments, the regenerating the output signature over time can inform a wound care treatment plan. The output signature, the regenerated output signature, and so on, can be useful for enabling medical evaluation such as skin assessment; wound assessment; wound assessment over time; treatment planning for wound care; infection detection; biochrome identification; respiratory infection detection; influenza detection; COVID-19 detection; residual cancer detection; oncological surgery residual cancer detection; oral hygiene detection such as detecting plaques, gingivitis, and other dental abnormalities; and so on. The generated and regenerated signatures can have applications in food recognition, food quality assessment, or food safety evaluation, detecting food adulteration, monitoring progression of fermentation, optimizing agricultural yield, and enabling field sobriety evaluation of individuals, to name just a few.

The system 1700 can include a computer program product embodied in a non-transitory computer readable medium for skin diagnostics, the computer program product comprising code which causes one or more processors to perform operations of: scanning a plurality of optical excitation light wavelength bands on a material sample, wherein the material sample exhibits optical spectral characteristics along the light wavelength spectrum; capturing excitation response wavelengths emitted by the material sample in response to the plurality of optical excitation light wavelength bands, wherein the capturing is accomplished using an imaging sensor; measuring output values of a plurality of pixels of an image from the imaging sensor, wherein the image represents excitation response wavelengths captured by the imaging sensor, wherein the measuring detects optical spectral characteristics of the material sample, and wherein the optical spectral characteristics are in response to the plurality of optical excitation light wavelength bands; and generating an output signature indicative of composition of the material sample, wherein the output signature is based on interpreting the output values that were measured.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions-generally referred to herein as a "circuit," "module," or "system" may be implemented by computer program instructions, by special-purpose hardware-based computer systems, by combinations of special purpose hardware and computer instructions, by combinations of general-purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are limited to neither conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

What is claimed is:

1. A method for skin diagnostics comprising:
scanning a plurality of optical excitation light wavelength bands on a material sample, wherein the material sample exhibits optical spectral characteristics along the light wavelength spectrum;
capturing excitation response wavelengths emitted by the material sample in response to the plurality of optical excitation light wavelength bands, wherein the capturing is accomplished using an imaging sensor, wherein the plurality of optical excitation light wavelength bands includes one or more non-fluorescent optical excitation light wavelength bands;
measuring output values of a plurality of pixels of an image from the imaging sensor, wherein the image represents excitation response wavelengths captured by the imaging sensor, wherein the measuring detects optical spectral characteristics of the material sample, and wherein the optical spectral characteristics are in response to the plurality of optical excitation light wavelength bands; and
generating an output signature indicative of composition of the material sample, wherein the output signature includes a granulation output signature for identifying granulation of the material sample, and wherein the output signature is based on interpreting the output values that were measured.

2. The method of claim 1 wherein the one or more non-fluorescent optical excitation light wavelength bands coincide with one or more absorption wavelength maximums of selected material constituents.

3. The method of claim 2, wherein the measuring output values includes measurements at the absorption wavelength maximums.

4. The method of claim 3, wherein the measurements at the absorption wavelength maximums augment the interpreting.

5. The method of claim 1 wherein a first band of the plurality of optical excitation light wavelength bands includes wavelengths in the range of 325 nm to 375 nm, a second band of the plurality of optical excitation light wavelength bands includes wavelengths in the range of 350 nm to 400 nm, and a third band of the plurality of optical excitation light wavelength bands includes wavelengths in the range of 375 nm to 425 nm.

6. The method of claim 5 wherein a fourth band of the plurality of optical excitation light wavelength bands includes wavelengths in the range of 400 nm to 450 nm.

7. The method of claim 6 wherein the interpreting is based on measured wavelengths in the range of 440 nm to 500 nm and 500 nm to 550 nm.

8. The method of claim 7 wherein the output signature is indicative of the presence of nicotinamide adenine dinucleotide plus hydrogen (NADH) and flavins.

9. The method of claim 5 wherein the interpreting is based on measured wavelengths in the range of 400 nm to 460 nm.

10. The method of claim 9 further comprising exposing the material sample to a fluorescence excitation light wavelength band comprising wavelengths in the 315 nm to 375 nm range to augment the interpreting.

11. The method of claim 1 wherein the plurality of optical excitation light wavelength bands comprises narrow bands at 350 nm, 375 nm, 400 nm, 425 nm, 450 nm, 500 nm, 525 nm, 550 nm, 575 nm, 600 nm, and 625 nm.

12. The method of claim 11 wherein the interpreting is based on measured wavelengths in the range of 600 nm to 660 nm and 675 nm to 725 nm.

13. The method of claim 12 wherein the output signature is indicative of the presence of porphyrins.

14. The method of claim 1 wherein the material sample includes cells, tissues, and organs.

15. The method of claim 14 wherein the material sample is from a wound.

16. The method of claim 15 wherein the output signature provides a wound healing trajectory.

17. The method of claim 15 further comprising regenerating the output signature over time.

18. The method of claim 17 wherein the regenerating the output signature over time informs a wound care treatment plan.

19. The method of claim 15 wherein the output signature enables infection detection.

20. The method of claim 19 wherein the output signature is based on fluorescence and reflectance images, and wherein the infection detection comprises comparing the output signature to a known spectral signature associated with infection.

21. The method of claim 15 wherein the output signature enables residual cancer detection.

22. The method of claim 1 further comprising spatially registering the image to determine wound features contained in the material sample, wherein the wound features include a wound center and a wound edge.

23. The method of claim 1 further comprising comparing image resolution at a plurality of narrow optical excitation light wavelength bands.

24. The method of claim 23 wherein the comparing enables wound depth analysis.

25. The method of claim 1 wherein the interpreting is based on excitation wavelengths from 380 nm to 420 nm and measured wavelengths in the range of 500 nm to 550 nm and 550 nm to 600 nm.

26. The method of claim 25 wherein the output signature is indicative of the presence of pyoverdine, based on a ratio of output values from the range of 550 nm to 600 nm to output values from the range of 500 nm to 550 nm.

27. The method of claim 1 wherein the plurality of optical excitation light wavelength bands comprises optical illumination.

28. The method of claim 27 wherein the optical illumination is provided by light emitting diodes (LEDs).

29. The method of claim 1 wherein a long-pass filter is disposed in front of the imaging sensor, and wherein the long-pass filter allows passage of visible light with a relative transmission amplitude of 0.9 out of 1.

30. A computer program product embodied in a non-transitory computer readable medium for skin diagnostics, the computer program product comprising code which causes one or more processors to perform operations of:
scanning a plurality of optical excitation light wavelength bands on a material sample, wherein the material sample exhibits optical spectral characteristics along the light wavelength spectrum;
capturing excitation response wavelengths emitted by the material sample in response to the plurality of optical excitation light wavelength bands, wherein the capturing is accomplished using an imaging sensor, wherein the plurality of optical excitation light wavelength bands includes one or more non-fluorescent optical excitation light wavelength bands;

measuring output values of a plurality of pixels of an image from the imaging sensor, wherein the image represents excitation response wavelengths captured by the imaging sensor, wherein the measuring detects optical spectral characteristics of the material sample, and wherein the optical spectral characteristics are in response to the plurality of optical excitation light wavelength bands; and generating an output signature indicative of composition of the material sample, wherein the output signature includes a granulation output signature for identifying granulation of the material sample, and wherein the output signature is based on interpreting the output values that were measured.

31. A computer system for skin diagnostics comprising:

a memory which stores instructions;

one or more processors coupled to the memory wherein the one or more processors, when executing the instructions which are stored, are configured to:

scan a plurality of optical excitation light wavelength bands on a material sample, wherein the material sample exhibits optical spectral characteristics along the light wavelength spectrum;

capture excitation response wavelengths emitted by the material sample in response to the plurality of optical excitation light wavelength bands, wherein the capturing is accomplished using an imaging sensor, wherein the plurality of optical excitation light wavelength bands includes one or more non-fluorescent optical excitation light wavelength bands;

measure output values of a plurality of pixels of an image from the imaging sensor, wherein the image represents excitation response wavelengths captured by the imaging sensor, wherein the measuring detects optical spectral characteristics of the material sample, and wherein the optical spectral characteristics are in response to the plurality of optical excitation light wavelength bands; and generate an output signature indicative of composition of the material sample, wherein the output signature includes a granulation output signature for identifying granulation of the material sample, and wherein the output signature is based on interpreting the output values that were measured.

* * * * *